(12) United States Patent
Huang et al.

(10) Patent No.: US 10,821,148 B2
(45) Date of Patent: Nov. 3, 2020

(54) PHARMACEUTICAL COMPOSITION FOR TREATING OR ALLEVIATING AN AUTOIMMUNE DISEASE AND/OR COMPLICATION THEREOF AND/OR NEPHRITIS AND METHOD FOR TREATING OR ALLEVIATING AN AUTOIMMUNE DISEASE AND/OR COMPLICATION THEREOF AND/OR NEPHRITIS

(71) Applicant: Industrial Technology Research Institute, Hsinchu (TW)

(72) Inventors: Kuo-Kuei Huang, Zhudong Township (TW); I-Horng Pan, Zhubei (TW); Ying-Fei Tsai, Hsinchu (TW); I-Huang Lu, Taipei (TW); Chu-Hsun Lu, Kaohsiung (TW); Shu-Fang Wen, Baoshan Township (TW); Zong-Keng Kuo, New Taipei (TW); Shu-Jiau Chiou, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 331 days.

(21) Appl. No.: 15/416,391

(22) Filed: Jan. 26, 2017

(65) Prior Publication Data
US 2017/0258865 A1 Sep. 14, 2017

Related U.S. Application Data

(60) Provisional application No. 62/287,330, filed on Jan. 26, 2016.

(51) Int. Cl.
| | |
|---|---|
| *A61K 36/00* | (2006.01) |
| *A61K 36/75* | (2006.01) |
| *A61K 31/395* | (2006.01) |
| *A61K 31/366* | (2006.01) |
| *A61K 31/37* | (2006.01) |
| *A61K 31/4015* | (2006.01) |
| *A61K 31/404* | (2006.01) |

(52) U.S. Cl.
CPC ............ *A61K 36/75* (2013.01); *A61K 31/366* (2013.01); *A61K 31/37* (2013.01); *A61K 31/395* (2013.01); *A61K 31/404* (2013.01); *A61K 31/4015* (2013.01)

(58) Field of Classification Search
CPC ..................................................... A61K 36/00
USPC ........................................................ 424/725
See application file for complete search history.

(56) References Cited

U.S. PATENT DOCUMENTS

| | | | |
|---|---|---|---|
| 8,486,914 B2 | 7/2013 | Wong et al. | |
| 9,066,965 B1 | 6/2015 | Kelley | |
| 9,266,926 B2 | 2/2016 | Shailubhai et al. | |
| 2002/0136784 A1* | 9/2002 | Obukowicz ............ | A61K 36/00 424/725 |
| 2004/0197429 A1 | 10/2004 | Obukowicz et al. | |
| 2011/0028428 A1* | 2/2011 | Wong ................... | A61K 31/715 514/54 |

FOREIGN PATENT DOCUMENTS

| | | |
|---|---|---|
| CN | 102139002 A | 8/2011 |
| CN | 103445121 A | 12/2013 |
| CN | 103461901 A | 12/2013 |
| CN | 103504013 A | 1/2014 |
| CN | 104054839 A | 9/2014 |
| CN | 104435491 A | 9/2014 |
| TW | 201334776 A1 | 9/2013 |
| WO | WO 2015/026205 A1 | 2/2015 |

OTHER PUBLICATIONS

Geng Tao Liu, et al., "Hepatoprotective Action of Nine Constituents Isolated From the Leaves of Clausena lansium in Mice.", Drug Development Research, vol. 39, 1996, pp. 174-178.
Taiwanese language Office Action and Search Report dated Mar. 2, 2018, issued in co-pending Taiwanese Application No. 106103202.
Adebajo, A.C., et al, "Pharmacological properties of the extract and some isloated compounds of Clausena lansium stem bark: Anti-trichomonal, antidiabetic, anti-inflammatory, hepatoprotective and antioxidant effects," J. Ethnopharmacol., 2009, vol. 122, pp. 10-19.
Amarilyo, G., et al, "IL-17 Promotes Murine Lupus," The Journal of Immunology, 2014, vol. 193, No. 2, pp. 540-543.
Cui, YX, et al, "Association of the interleukin-6 polymorphisms with systemic lupus erythematosus: a meta-analysis," Lupus, 2015, vol. 24, No. 12, pp. 1308-1317.
Gaffen, S. L., et al, "The IL-23-IL-17 immune axis: from mechanisms to therapeutic testing," Nature Reviews Immunology, Sep. 2014, vol. 14, No. 9, pp. 585-600.
Galil, S., et al, "The role of serum IL-17 and IL-6 as biomarkers of disease activity and predictors of remission in patients with lupus nephritis," Cytokine, 2015, vol. 76, No. 2, pp. 280-287.
Hammad, A., et al, "Interleukin-17A rs2275913, Interleukin-17F rs763780 and rs2397084 gene polymorphisms as possible risk factors in Juvenile lupus and lupus related nephritis," Autoimmunity, 2015, pp. 1-10.
Jin, W., et al, "IL-17 cytokines in immunity and inflammation," Emerging Microbes & Infections, 2013, vol. 2 , p. e60.
Li, D., et al, "Interleukin-17 in systemic lupus erythematosus: A comprehensive review," Autoimmunity, 2015, pp. 1-9.

(Continued)

*Primary Examiner* — Michael V Meller
(74) *Attorney, Agent, or Firm* — Birch, Stewart, Kolasch & Birch, LLP

(57) ABSTRACT

The present disclosure provides a pharmaceutical composition for treating or alleviating an autoimmune disease and/or complication thereof and/or nephritis, including: an effective amount of an extract of a plant belonging to *Rutaceae* as an effective ingredient for treating or alleviating the autoimmune disease and/or complication thereof and/or nephritis, wherein the autoimmune disease is selected from a group consisting of lupus erythematosus, psoriasis, psoriatic arthritis, ankylosing spondylitis, rheumatoid arthritis, juvenile idiopathic arthritis, Crohn's disease and ulcerative colitis (UC).

8 Claims, 29 Drawing Sheets

(56) References Cited

OTHER PUBLICATIONS

Matsui, T., et al, "Lansiumamide B and SB-204900 isolated from Clausena lansium inhibit histamine and TNF-α release from RBL-2H3 cells," Inflamm Res, 2013, vol. 62, pp. 333-341.

Peliçari, K., et al, "Serum interleukin-17 levels are associated with nephritis in childhood-onset systemic lupus erythematosus," Clinics, 2015, vol. 70, No. 5, pp. 313-317.

Ramani, K., et al, "Emerging roles of the Th17/IL-17-axis in glomerulonephritis," Cytokine, 2016, vol. 77, pp. 238-244.

Ramani, K., et al, "Interleukin 17 signaling drives Type I Interferon induced proliferative crescentic glomerulonephritis in lupus-prone mice," Clinical Immunology, 2016, vol. 162, pp. 31-36.

Solus, J.F., et al, "Genetics of serum concentration of IL-6 and TNFα in systemic lupus erythematosus and rheumatoid arthritis: a candidate gene analysis," Clinical rheumatology, 2015, pp. 1-8.

Tahghighi, F., et al, "Tumor necrosis factor-alpha single nucleotide polymorphisms in juvenile systemic lupus erythematosus," Human Immunology, 2015, vol. 76, No. 8, pp. 533-536.

Watanabe, R., et al, "Chronic Lupus Peritonitis is Characterized by the Ascites with a Large Content of Interleukin-6," Tohoku J. Exp. Med., 2015, vol. 235, No. 4, pp. 289-294.

Zickert, A., et al, "IL-17 and IL-23 in lupus nephritis-association to histopathology and response to treatment," BMC Immunology, 2015, vol. 16, No. 7, pp. 1-10.

Jiang, H.Y., et al, "Cytotoxic Constituents from the Stems of Clausena lansium (Lour.) Skeels," Molecules, 2013, vol. 18, pp. 10768-10775.

Mbah, J.A., et al, "Antibacterial Agents from the Seeds of *Peucedanum zenkeri* L. (Umbelliferae)," Pak J Med Sci, 2010, vol. 26, No. 2, pp. 314-318.

Rodanant, P., et al, "In vitro evaluation of the antibacterial and anti-inflammation activities of Clausena lansium (Lour.) Skeels," Songklanakarin J. Sci. Technol., 2015, vol. 37, No. 1, pp. 43-48.

Taiwanese Office Action for Appl. No. 106103202 dated Aug. 17, 2018.

\* cited by examiner

PHARMACEUTICAL COMPOSITION FOR TREATING OR ALLEVIATING AN AUTOIMMUNE DISEASE AND/OR COMPLICATION THEREOF AND/OR NEPHRITIS AND METHOD FOR TREATING OR ALLEVIATING AN AUTOIMMUNE DISEASE AND/OR COMPLICATION THEREOF AND/OR NEPHRITIS

CROSS REFERENCE TO RELATED APPLICATION

This application claims the benefit of U.S. Provisional Application No. 62/287,330, filed on Jan. 26, 2016, the entirety of which is incorporated by reference herein.

TECHNICAL FIELD

The present disclosure relates to a pharmaceutical composition for treating or alleviating an autoimmune disease and/or a complication thereof and/or nephritis and a method for treating or alleviating an autoimmune disease and/or a complication thereof and/or nephritis.

BACKGROUND

An autoimmune disease is a disease in which the immune system of the human body attacks normal cells in the body. In the body of a patient with an autoimmune disease, the immune system will produce antibodies against normal cells (even various normal components of a cell) in the body, and that results in abnormal and excess inflammatory response and tissue injury, and thus affects the health of the body.

Moreover, autoimmune diseases, such as lupus erythematosus, usually affect multiple organs, including brain, lungs and kidney. The definite etiology resulting in lupus erythematosus is still unclear, and it may be related to genes, hormones, environments and infections. Although since the 1950s, the mortality rate of lupus erythematosus has gradually decreased, patients still suffer from recurrent episodes of the illness.

Therefore, there is a need to develop a more effective drug for treating autoimmune diseases, such as lupus erythematosus.

SUMMARY

The present disclosure provides a pharmaceutical composition for treating or alleviating an autoimmune disease and/or a complication thereof and/or nephritis, comprising: an effective amount of an extract of a plant belonging to *Rutaceae* as an effective ingredient for treating or alleviating the autoimmune disease and/or a complication thereof and/or nephritis, wherein the autoimmune disease is selected from a group consisting of lupus erythematosus, psoriasis, psoriatic arthritis, ankylosing spondylitis, rheumatoid arthritis, juvenile idiopathic arthritis, Crohn's disease and ulcerative colitis (UC).

The present disclosure also provides a method for treating or alleviating an autoimmune disease and/or a complication thereof and/or nephritis, comprising: administering an effective amount of an extract of a plant belonging to *Rutaceae* to a subject in need thereof to treat or alleviate the autoimmune disease and/or a complication thereof and/or nephritis, wherein the extract of a plant belonging to *Rutaceae* is an effective ingredient for treating or alleviating the autoimmune disease and/or a complication thereof and/or nephritis, and wherein the autoimmune disease is selected from a group consisting of lupus erythematosus, psoriasis, psoriatic arthritis, ankylosing spondylitis, rheumatoid arthritis, juvenile idiopathic arthritis, Crohn's disease and ulcerative colitis (UC).

The present disclosure further provides another pharmaceutical composition for treating or alleviating an autoimmune disease and/or a complication thereof and/or nephritis, comprising: an effective amount of a compound as an effective ingredient for treating or alleviating the autoimmune disease and/or a complication thereof and/or nephritis, wherein the compound is at least one compound selected from a group consisting of:

(a) a compound having Formula (I):

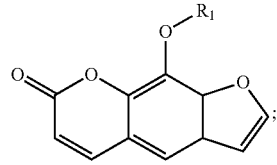

Formula (I)

(b) a compound having Formula (II):

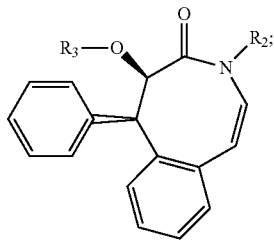

Formula (II)

and
(c) a compound having Formula (II):

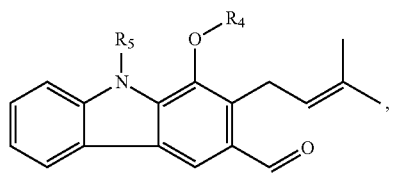

Formula (III)

wherein $R_1$ is $C_1$-$C_5$ alkyl,

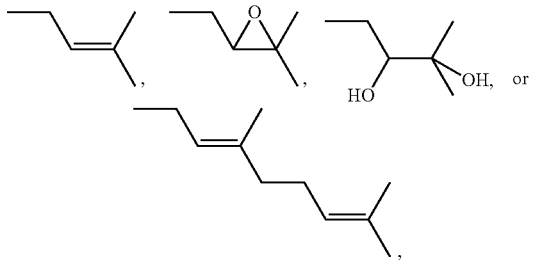

$R_2$ is H or $C_1$-$C_3$ alkyl, $R_3$ is H or $C_1$-$C_3$ alkyl, $R_4$ is H or $C_1$-$C_3$ alkyl, and $R_5$ is H or $C_1$-$C_3$ alkyl.

The present disclosure further provides a method for treating or alleviating an autoimmune disease and/or a complication thereof and/or nephritis, comprising: administering an effective amount of a compound to a subject in need thereof to treat or alleviate the autoimmune disease and/or a complication thereof and/or nephritis, wherein the compound is at least one compound selected from a group consisting of:

(a) a compound having Formula (I):

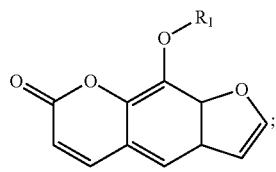

Formula (I)

(b) a compound having Formula (II):

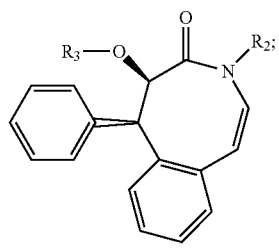

Formula (II)

and
(c) a compound having Formula (II):

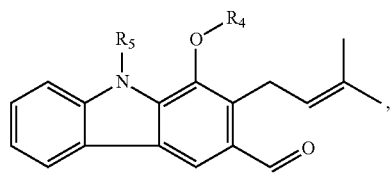

Formula (III)

wherein $R_1$ is $C_1$-$C_5$ alkyl,

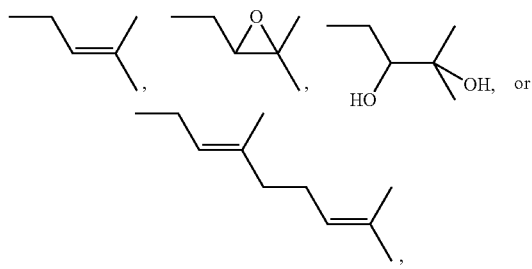

$R_2$ is H or $C_1$-$C_3$ alkyl, $R_3$ is H or $C_1$-$C_3$ alkyl, $R_4$ is H or $C_1$-$C_3$ alkyl, and $R_5$ is H or $C_1$-$C_3$ alkyl, wherein the compound is an effective ingredient for treating or alleviating the autoimmune disease and/or a complication thereof and/or nephritis.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
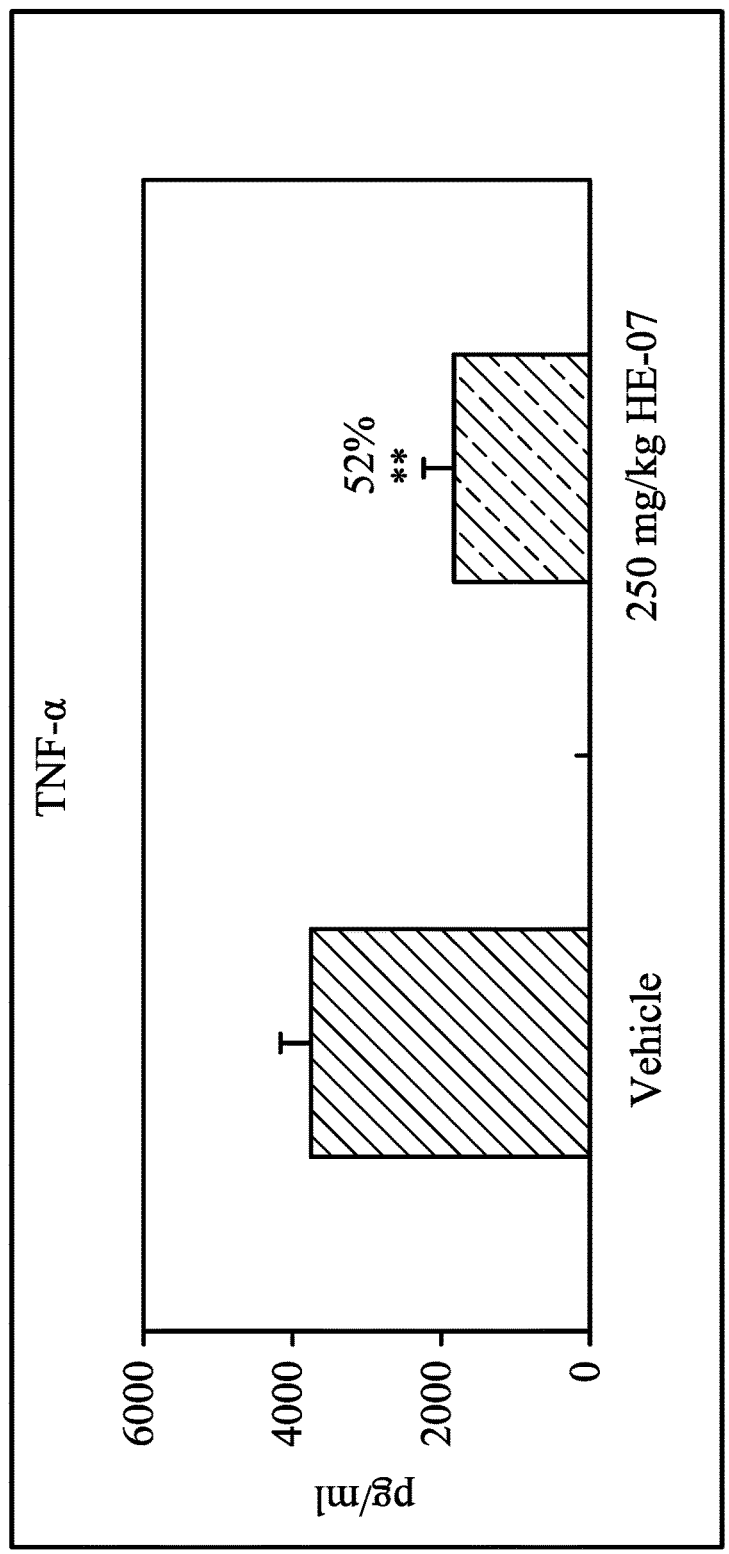
FIG. 1A shows the effects of the ethanol extract of *Clausena lansium* (HE-07) on production of the inflammatory factor, TNF-α, in the model of lipopolysaccharide (LPS)-induced acute inflammation in mice.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a pharmaceutical composition for treating or alleviating an autoimmune disease and/or a complication thereof and/or nephritis, which is capable of inhibiting IL-17 production and inhibiting inflammation, and has the effects of treating or alleviating an autoimmune disease and/or a complication thereof and/or nephritis. Examples of the above-mentioned autoimmune disease may include, but are not limited to, lupus erythematosus, psoriasis, psoriatic arthritis, ankylosing spondylitis, rheumatoid arthritis, juvenile idiopathic arthritis, Crohn's disease and ulcerative colitis (UC).

The above-mentioned pharmaceutical composition for treating or alleviating an autoimmune disease and/or a complication thereof and/or nephritis of the present disclosure, may include, but is not limited to, an effective amount of an extract of a plant belonging to Rutaceae, wherein the extract of a plant belonging to *Rutaceae* is an effective ingredient for treating or alleviating the autoimmune disease and/or a complication thereof and/or nephritis. In one embodiment, the pharmaceutical composition for treating or alleviating an autoimmune disease and/or a complication thereof and/or nephritis of the present disclosure may further include a pharmaceutically acceptable carrier or salt.

In the pharmaceutical composition of the present disclosure mentioned above, the plant belonging to *Rutaceae* mentioned above may include a plant belonging to genus *Clausena,* a plant belonging to genus *Murraya* or a plant belonging to genus *Citrus,* but it is not limited thereto. Moreover, examples of the above-mentioned plant belonging to *Clausena* may include, but are not limited to, *Clausena lansium* and *Clausena excavata* Burm. f. Examples of the above-mentioned plant belonging to *Murraya* may include, but are not limited to, *Murraya euchrestifolia* and *Murraya paniculata.* Examples of the above-mentioned plant belonging to *Citrus* may include, but are not limited to, *Citrus grandis* and *Citrus tankan*.

In the pharmaceutical composition of the present disclosure mentioned above, the extract of a plant belonging to *Rutaceae* may be obtained by extracting a plant belonging to *Rutaceae* with an alcohol (for example, methanol, ethanol or propanol), an ester (for example, ethyl acetate), an alkane (for example, hexane) or a haloalkane (for example, chloromethane, chloroethane), but it is not limited thereto. In one embodiment, the extract of a plant belonging to *Rutaceae* may be obtained by extracting a plant belonging to *Rutaceae* with ethanol.

In one embodiment, in the pharmaceutical composition of the present disclosure mentioned above, the foregoing extract of a plant belonging to *Rutaceae* is an ethanol extract of *Clausena lansium*. In this embodiment, indicator ingredients of the ethanol extract of *Clausena lansium* may include O-methylheracleno, prangenin, ζ-clausenamide, imperatorin, 8-geranyloxypsoralen and indizoline, but they are not limited thereto. Moreover, in this embodiment, an effective ingredient for treating or alleviating an autoimmune disease and/or a complication thereof and/or nephritis in the ethanol extract of *Clausena lansium* may include prangenin, ζ-clausenamide, imperatorin, 8-geranyloxypsoralen, indizoline, or any combination thereof, but it is not limited thereto.

In the foregoing embodiment in which the extract of a plant belonging to Rutaceae mentioned above is an ethanol extract of *Clausena lansium*, the pharmaceutical composition of the present disclosure can be used to treat or alleviate lupus erythematosus. Furthermore, the above-mentioned lupus erythematosus may be systemic lupus erythematosus. Moreover, in this embodiment, the pharmaceutical composition of the present disclosure can be used to treat or alleviate a complication of lupus erythematosus, such as lupus nephritis. Furthermore, in this embodiment, pharmaceutical composition of the present disclosure also can be used to treat or alleviate a common nephritis.

The present disclosure also provides a pharmaceutical composition for treating or alleviating an autoimmune disease and/or a complication thereof and/or nephritis which uses a compound as a main effective ingredient.

The above-mentioned pharmaceutical composition for treating or alleviating an autoimmune disease and/or a complication thereof and/or nephritis, may include, but is not limited to, an effective amount of a compound which is an effective ingredient for treating or alleviating the autoimmune disease and/or a complication thereof and/or nephritis, wherein the compound mentioned above may be at least one selected from the compounds shown in the following:

(a) a compound having Formula (I):

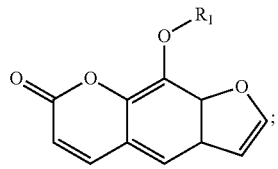

Formula (I)

(b) a compound having Formula (II):

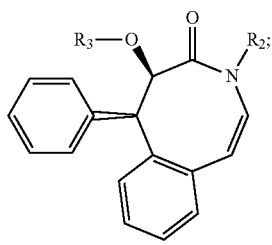

Formula (II)

and
(c) a compound having Formula (II):

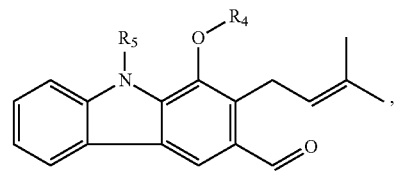

Formula (III)

wherein $R_1$ is $C_1$-$C_5$ alkyl,

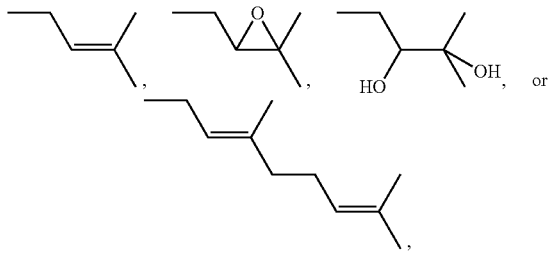

, , , or $R_2$ is H or $C_1$-$C_3$ alkyl, $R_3$ is H or $C_1$-$C_3$ alkyl, $R_4$ is H or $C_1$-$C_3$ alkyl, and $R_5$ is H or $C_1$-$C_3$ alkyl.

In addition, examples of the above-mentioned autoimmune disease may include lupus erythematosus, psoriasis, psoriatic arthritis, ankylosing spondylitis, rheumatoid arthritis, juvenile idiopathic arthritis, Crohn's disease, and ulcerative colitis (UC), but they are not limited thereto.

In one embodiment, the above-mentioned pharmaceutical composition for treating or alleviating an autoimmune disease and/or a complication thereof and/or nephritis of the present disclosure may further include a pharmaceutically acceptable carrier or salt.

Moreover, in the above-mentioned pharmaceutical composition for treating or alleviating an autoimmune disease and/or a complication thereof and/or nephritis of the present disclosure, examples of the compound having Formula (I) may include prangenin, imperatorin, and 8-geranyloxypsoralen, but they are not limited thereto. Examples of the compound having Formula (II) may include, but they are not limited to, ζ-clausenamide. Examples of the compound having Formula (III) may include indizoline, but they are not limited thereto.

In one embodiment, in the above-mentioned pharmaceutical composition for treating or alleviating an autoimmune disease and/or a complication thereof and/or nephritis of the present disclosure, the compound having Formula (I) may be prangenin, imperatorin or 8-geranyloxypsoralen, the compound having Formula (II) may be ζ-clausenamide, and the compound having Formula (III) may be indizoline.

In another embodiment, in the above-mentioned pharmaceutical composition for treating or alleviating an autoimmune disease and/or a complication thereof and/or nephritis of the present disclosure, the compound having Formula (I) is an effective ingredient. In this embodiment, the pharmaceutical composition of the present disclosure can be used to treat or alleviate lupus erythematosus. The above-mentioned lupus erythematosus may be systemic lupus erythematosus. Moreover, in this embodiment, the pharmaceutical composition of the present disclosure may be used to treat or alleviate a complication of lupus erythematosus, such as lupus nephritis. In addition, in this embodiment, the pharmaceutical composition of the present disclosure may be used to treat or alleviate a common nephritis. In a specific embodiment, the compound having Formula (I) mentioned above is 8-geranyloxypsoralen.

In the any above-mentioned pharmaceutical composition for treating or alleviating an autoimmune disease and/or a complication thereof and/or nephritis of the present disclosure, the pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Moreover, the pharmaceutically acceptable salt mentioned above may include, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

The pharmaceutical composition of the present disclosure may be administered orally, parenterally by an inhalation spray, or via an implanted reservoir. The parenteral methods may comprise subcutaneous, intracutaneous, intravenous, intramuscular, intra-articular, intra-arterial, intrasynovial, intrasternal, intrathecal, and intraleaional, as well as infusion techniques.

An oral composition may include, but is not limited to, tablets, capsules, emulsions, and aqueous suspensions, dispersions and solutions.

Moreover, the present disclosure further provides a method for treating or alleviating an autoimmune disease and/or a complication thereof and/or nephritis. The method may include, but is not limited to, administering an effective amount of an extract of a plant belonging to *Rutaceae* to a subject in need thereof to treat or alleviate the autoimmune disease and/or a complication thereof and/or nephritis.

The above-mentioned extract of a plant belonging to *Rutaceae* has the effects of inhibiting IL-17 production, inhibiting inflammation, etc., and may be an effective ingredient for treating or alleviating an autoimmune disease and/or a complication thereof and/or nephritis. Furthermore, the above-mentioned autoimmune disease may include lupus erythematosus, psoriasis, psoriatic arthritis, ankylosing spondylitis, rheumatoid arthritis, juvenile idiopathic arthritis, Crohn's disease or ulcerative colitis (UC), etc., but it is not limited thereto.

In addition, the above-mentioned plant belonging to *Rutaceae* may include a plant belonging to *Clausena*, a plant belonging to *Murraya* or a plant belonging to *Citrus*, but it is not limited thereto. Examples of the above-mentioned plant belonging to *Clausena* may include, but are not limited to, *Clausena lansium* and *Clausena excavata* Burm. f Examples of the above-mentioned plant belonging to *Murraya* may include, but are not limited to, *Murraya euchrestifolia* and *Murraya paniculata*. Furthermore, examples of the above-mentioned plant belonging to *Citrus* may include, but are not limited to, *Citrus grandis* and *Citrus tankan*.

In addition, the extract of a plant belonging to *Rutaceae* mentioned above may be obtained by extracting a plant belonging to *Rutaceae* with an alcohol (for example, methanol, ethanol or propanol), an ester (for example, ethyl acetate), an alkane (for example, hexane) or a haloalkane (for example, chloromethane, chloroethane), but it is not limited thereto. In one embodiment, the extract of a plant belonging to *Rutaceae* may be obtained by extracting a plant belonging to *Rutaceae* with ethanol.

In one embodiment, the extract of a plant belonging to *Rutaceae* mentioned above is an ethanol extract of *Clausena lansium*. In this embodiment, indicator ingredients of the ethanol extract of *Clausena lansium* may include O-methylheracleno, prangenin, ζ-clausenamide, imperatorin, 8-geranyloxypsoralen and indizoline, but they are not limited thereto. Moreover, in this embodiment, an effective ingredient for treating or alleviating an autoimmune disease and/or a complication thereof and/or nephritis in the ethanol extract of *Clausena lansium* may include prangenin, ζ-clausenamide, imperatorin, 8-geranyloxypsoralen, indizoline or any combination thereof, but it is not limited thereto.

In the embodiment mentioned above in which the extract of a plant belonging to *Rutaceae* mentioned above is an ethanol extract of *Clausena lansium,* the above-mentioned method for treating or alleviating an autoimmune disease and/or a complication thereof and/or nephritis of the present disclosure can be used to treat or alleviate lupus erythematosus. The above-mentioned lupus erythematosus may be systemic lupus erythematosus. Moreover, in this embodiment, the method for treating or alleviating an autoimmune disease and/or a complication thereof and/or nephritis of the present disclosure can be used to treat or alleviate a complication of lupus erythematosus, such as lupus nephritis. Furthermore, in this embodiment, the method for treating or alleviating an autoimmune disease and/or a complication thereof and/or nephritis of the present disclosure can be used to treat or alleviate a common nephritis.

In addition, the present disclosure also provides another method for treating or alleviating an autoimmune disease and/or a complication thereof and/or nephritis. The above-mentioned method may include, but is not limited to, administering an effective amount of a compound to a subject in need thereof to treat or alleviate the autoimmune disease and/or a complication thereof and/or nephritis, and the compound mentioned above may be at least one selected from the compounds shown in the following:

(a) a compound having Formula (I):

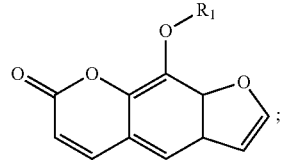

Formula (I)

;

(b) a compound having Formula (II):

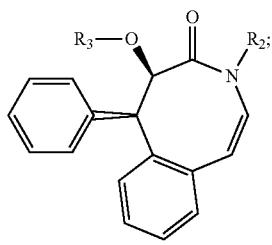

Formula (II)

and
(c) a compound having Formula (II):

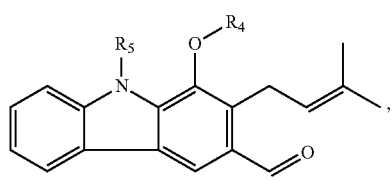

Formula (III)

wherein $R_1$ is $C_1$-$C_5$ alkyl,

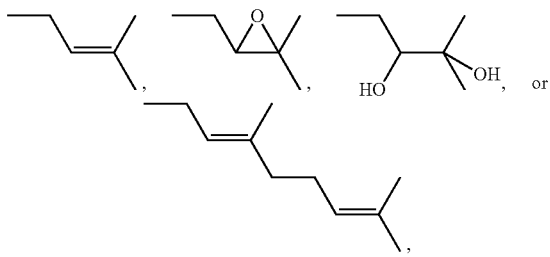

$R_2$ is H or $C_1$-$C_3$ alkyl, $R_3$ is H or $C_1$-$C_3$ alkyl, $R_4$ is H or $C_1$-$C_3$ alkyl, and $R_5$ is H or $C_1$-$C_3$ alkyl.

The above-mentioned compound may be an effective ingredient for treating or alleviating an autoimmune disease and/or a complication thereof and/or nephritis. Furthermore, examples of the above-mentioned autoimmune disease may include lupus erythematosus, psoriasis, psoriatic arthritis, ankylosing spondylitis, rheumatoid arthritis, juvenile idiopathic arthritis, Crohn's disease, and ulcerative colitis (UC), but they are not limited thereto.

Examples of the compound having Formula (I) may include prangenin, imperatorin, and 8-geranyloxypsoralen, but they are not limited thereto. Examples of the compound having Formula (II) may include, but are not limited to, ζ-clausenamide. In addition, examples of the compound having Formula (III) may include indizoline, but they are not limited thereto.

In one embodiment, in the above-mentioned method for treating or alleviating an autoimmune disease and/or a complication thereof and/or nephritis of the present disclosure, the compound having Formula (I) may be prangenin, imperatorin or 8-geranyloxypsoralen, the compound having Formula (II) may be ζ-clausenamide, and the compound having Formula (III) may be indizoline.

Furthermore, in one embodiment, in the above-mentioned method for treating or alleviating an autoimmune disease and/or a complication thereof and/or nephritis of the present disclosure, the above-mentioned compound having Formula (I) is an effective ingredient. In this embodiment, the above-mentioned method for treating or alleviating an autoimmune disease and/or a complication thereof and/or nephritis of the present disclosure can be used to treat or alleviate lupus erythematosus. The foregoing lupus erythematosus may be systemic lupus erythematosus. Moreover, in this embodiment, the above-mentioned method for treating or alleviating an autoimmune disease and/or a complication thereof and/or nephritis of the present disclosure can be used to treat or alleviate a complication of lupus erythematosus, such as lupus nephritis. In addition, in this embodiment, the above-mentioned method for treating or alleviating an autoimmune disease and/or a complication thereof and/or nephritis of the present disclosure may be used to treat or alleviate a common nephritis. In a specific embodiment, the compound having Formula (I) mentioned above is 8-geranyloxypsoralen.

In any above-mentioned method for treating or alleviating an autoimmune disease and/or a complication thereof and/or nephritis of the present disclosure, the subject may include a mammal, but it is not limited thereto. Examples of the mammal may include, but are not limited to, a human, an orangutan, a monkey, a horse, a donkey, a dog, a cat, a rabbit, a guinea pig, a rat, and a mouse. In one embodiment, in any above-mentioned method for treating or alleviating an autoimmune disease and/or a complication thereof and/or nephritis of the present disclosure, the subject is a human.

EXAMPLES

A. Material and Method

1. Method 1: Preparation of Ethanol Extracts of Medicinal Herbs

After being washed or dried, medicinal herb was pulverized. 500 g of medicinal herb powder was added to 5-fold volume of 95% ethanol and extracted in a shaker at 25° C. for a week. The obtained extract solution was vacuum-filtered to obtain a filtrate and quantify the volume thereof. After that, 2 mL of the filtrate was sampled to perform high-performance liquid chromatography (HPLC) and thin layer chromatography (TLC).

The remaining filtrate was vacuum-filtered to a volume of about 30 mL and then was divided into portions to package in freeze drying vials and lyophilized, and the obtained lyophilized product was the drug to be tested (extraction ratio: about 3.5%).

2. Method 2: Anti-IL-17 Secretion Drug Screening Through a Peripheral Blood Leukocyte (PBL) Platform Blood of SD rat was obtained through saphenous vein sampling. The rat blood was placed in a centrifuge tube containing EDTA (final concentration was 2 mg/ml) and mixed well, and then 4-fold volume of ACK buffer was added to the centrifuge tube to lyse red blood cells. The above-mentioned centrifuge tube was placed in a 37° C. water bath for 5 minutes, and 4 folds volume of PBS buffer was added to the centrifuge tube and the centrifuge tube was centrifuged at a speed of 3000 rpm for 5 minutes, and the supernatant was removed. After that, the steps for lysing red blood cells were repeated twice and an appropriate volume of cell culture medium was added to the centrifuge.

The cells was implanted to a 96-well plate ($2\times10^5$ cells/well), and an appropriate concentration of a drug to be tested was added therein (10 μl/well) and evenly mixed. Next, the 96-well plate was placed in an incubator at 37° C. with 5% $CO_2$ for 1 hour. After that, the stimuli, phorbol-12-myristate- 13-acetate (PMA) (final concentration was 30 ng/ml), and ionomycin (final concentration was 1 µg/ml) were added to the 96-well plate. After being evenly mixed, the 96-well plate was placed in an incubator for 48 hours.

After 48 hours of culturing, the 96-well plate was centrifuged at 3000 rpm for 5 minutes to let the cells precipitate and the supernatant (cell-cultured medium) was transferred to a new 96-well plate (about 155 µl/well).

Alamar Blue was added to the cells that remained in the original 96-well plate (5 µl/well), and the original 96-well plate was placed in an incubator at 37° C. with 5% $CO_2$ for 4 hours. After that, cell viability was determined by an ELISA reader with excitation light 560 nm and emission light 590 nm.

After the cell-cultured medium in the new 96 well plate was 2-4 fold diluted, a rat IL-17 ELISA kit (eBioscience, 88-7170) was used to determine IL-17 content thereof.

For both of cell viability assay and IL-17 content assay, the result of the group adding phorbol-12-myristate-13-acetate (PMA) and ionomycin was set as 100%, and secretion of IL-17 was shown by percentage.

Method 3: Th17 Differentiation Assay

C57BL/6 mice were purchased from the National Laboratory Animal Center (Taiwan) and then bred in the Animal station of the Industrial Technology Research Institute. The standards of experimental animal and experimental operation (ITRI-IACUC-2012-025) used in the Animal station of the Industrial Technology Research Institute were followed.

Spleens of 6-8 week old C57BL/6 mice were exteriorized. After that, the spleens were ground with a Falcon® Cell Strainer (CORNING), and cell suspension was collected to be the primary spleen cells. Next, CD4+ T cells were isolated from the primary spleen cells by using IMag magnetic system (BD Pharmingen) according to the manufacturer's instructions.

Then, the CD4+ T cells were added to a 24-well cell culture plate ($5 \times 10^5$ cells/well) on which anti-CD3 (1 µg/ml; eBioscience) had to be coated on the previous day. After that, anti-CD28 (eBioscience) was added to the 24-well cell culture plate to active T cells, and simultaneously, IL-6 (PEPROTECH), TGF-β (PEPROTECH), anti-IFN-γ (eBioscience), anti-IL-4 (eBioscience) and anti-IL-2 (eBioscience) were added to the 24-well cell culture plate to perform Th17 cell differentiation, and finally, the sample to be tested was added. After that, the 24-well cell culture plate was placed in an incubator at 37° C. with 5% $CO_2$ for 3 days.

After 3 day culturing, the 24-well plate was centrifuged at 1100 rpm for 5 minutes to let the cells precipitate and the supernatant (cell-cultured medium) was transferred to a new 24-well plate (950 µl/well).

Alamar Blue (AbD Serotec) was added to the cells that remained in the original 24-well plate (20 µl/well), and the original 24-wellplate was placed in an incubator at 37° C. with 5% $CO_2$ for 6 hours. After the above-mentioned culturing, absorbance of cells at wavelengths of 570 nm and 600 nm was determined by a continuous wavelength microplate reader, and cell viability was calculated according to the analysis formula suggested by the manufacturer.

The cell-cultured medium mentioned above was 5-fold diluted and the IL-17 content thereof was analyzed by a commercial Mouse IL-17A ELISA Ready-SET-Go!® (eBioscience) according to the manufacturer's instructions.

4. Method 4: Inducing of CXCL9 by IFN-γ in Monocytes

Human monocytic cells (THP-1) were obtained from Bioresource Collection and Research Center (BCRC) (Taiwan). First, THP-1 cells ($2 \times 10^4$/mL) were seeded in a 96-well culture plate. The 96-well culture plate was placed in an incubator at 37° C. with 5% $CO_2$ for 16 hours, and then recombinant human IFN-γ (1 mg/ml) and a sample to be tested were added to the 96-well culture plate and co-cultured for 24 hours.

After 24 hours of culturing, the 96-well plate was centrifuged at 1100 rpm for 3 minutes to let the cells precipitate and the supernatant (cell-cultured medium) was transferred to a new 96-well plate (90 µl/well).

Alamar Blue (AbDSerotec; Cat. No. BUF012B) was added to the original 96-well plate, and the original 96-well plate was placed in an incubator at 37° C. with 5% $CO_2$ for 4 hours. After the above-mentioned culturing, absorbance of cells at wavelengths of 570 nm and 600 nm was determined by a continuous wavelength microplate reader, and cell viability was calculated according to the following formula:

Cell viability=(11,726×Experimental group $OD_{570}$)−(80,586×Experimental group $OD_{600}$)/(11,726×Control group $OD_{570}$)−(80,586×Control group $OD_{600}$)×100%, wherein, 11,726 and 80,586 are molar absorptivity of alamar Blue at $OD_{570}$ and $OD_{600}$, respectively.

The CXCL9 concentration of the cell-cultured medium was analyzed by using human CXCL9/MIG DuoSet ELISA (R&D; Cat. No. DY392) according to the manufacturer's instructions.

5. Method 5: Model of Lipopolysaccharide (LPS)-Induced Acute Inflammation in Mice 5.1 BALB/c Mice 6-8 weeks old male BALB/c mice were purchased from BioLASCO Taiwan Co., Ltd. On the day that the animals entered, the mice were marked, separated into cages, and weighed. Then, the mice were quarantined for one week, and the breeding conditions meet the standards of the National Laboratory Animal Center (Taiwan). During the quarantine, the motility and environmental adaptability of the mice were observed. If the body weights of the mice increased normally, the mice were moved to the breeding region to await the implementation of the experiment.

Illumination for the breeding region was automatically controlled for 12-hr light-dark cycle, and the temperature was controlled at 23±2° C. The animals were free to obtain sufficient food and water. This strain of animals has had abundant basic reference information and data, and can be suitable for a functional evaluation test for inflammation, and the experimental method had been approved by Institutional Animal Care and Use Committees (IACUC) in the Industrial Technology Research Institute.

5.2 Treatment of the Mice

Before the experiment, the mice were weighed and grouped to make the average body weight for each group has no obvious difference, and the clinical symptoms of the mice were recorded. Two to four hours before the experiment, the mice were fasting, but water was still regularly provided. At a specific time before or after being stimulated by lipopolysaccharides (LPS), the mice were administered a drug to be tested through oral administration, intraperitoneal injection (IP) or intravenous injection (IV), and after the administration, the clinical symptoms of the mice were observed and recorded. The mice of the control group were administered the same volume of solvent. The mice were stimulated by 1 mg/kg lipopolysaccharides (0.25 ml/mouse) through intraperitoneal injection (IP), and the clinical symptoms of the mice were observed and recorded.

After being stimulated by lipopolysaccharides for 1.5 hours, the mice were euthanized with excess $CO_2$, and then whole blood of the mice was obtained through intra-cardiac puncture.

The whole blood of the mice was centrifuged at 6000 rpm at 4° C. for 10 minutes. After that, plasma was collected, and determinations of TNF-α, IL-6 and MCP-1 secretion amounts in the plasma were performed.

5.3 Determinations of TNF-α, IL-6 and MCP-1 Secretion Amounts

TNF-α, IL-6 and MCP-1 secretion amounts in the plasma were analyzed according to the analysis steps of Duoset® ELISA kit, and the steps are summarized as follows:

At room temperature, a capture antibody mixture solution was added to an ELISA 96 well plate (100 μl/well) to cover the surface of the ELISA 96-well plate. After standing overnight, the mixture solution was sucked out and the ELISA 96-well plate was washed with Wash Buffer (300 μl/well) for three times, and then Block buffer was added to the ELISA 96-well plate (200 μl/well) to cover the remained space and the reaction was carried out at room temperature for 1 hour. The washing steps mentioned above were repeated.

Next, a sample to be tested which is diluted with appropriate fold and a standard were added to the ELISA 96-well plate (100 μl/well), and the reaction was carried out at room temperature for 2 hours. Then, the washing steps mentioned above were repeated.

After washing, a detection antibody mixture solution was added to the ELISA 96-well plate (100 μl/well), and the reaction was carried out at room temperature for 2 hours. The washing steps mentioned above were repeated.

Streptavidin-horseradish peroxidase (Streptavidin-HRP) mixture solution was added to the ELISA 96-well plate (100 μl/well), and the reaction was carried out at room temperature in darkness for 20 minutes. The washing steps mentioned above were repeated.

After that, Substrate Solution (TMB) was added to the ELISA 96-well plate (100 μl/well), and the reaction was carried out at room temperature in darkness for 20 minutes. Finally, Stop Solution (1N HCl) was added to the ELISA 96-well plate (50 μl/well) to terminate the color reaction, and absorbance at 450 nm (OD 450nm) was determined.

5.4 Statistical Analysis

The data of this experiment was shown by Mean±Standard error (S.E.) of the experimental result. The t-test was adopted to determine whether there was difference between each group, and if the p-value is less than 0.05, it means that the two testing groups have statistically significant differences.

6. Method 6: NZBWF Autoimmune Animal Model for Systemic Lupus Erythematosus (SLE)

6.1 NZBWF1/J Female Mice

NZBWF1/J female mice were purchased from The Jackson Laboratory, U.S.A, and after animal quarantine, the mice were fed to an appropriate age (about 16 to 25 weeks old).

Before the experiment, mice were randomly grouped according to the antibody to double stranded DNA (dsDNA) value of sera, then the mice were started to administrate test articles. Mice were administrated 5 days a week, and after 10-18 weeks of continuous administration, the mice were sacrificed. During the administration, body weight change was recorded every week, mice urine were collected every 1 to 2 week by gently pressing the abdomens of the mice and the urinary protein content (mg/dl) was determined by test strips and a protein quantitative kit.

After the experiment was completed, the urine was collected and the whole blood of the mice was obtained through intra-cardiac puncture. After that, kidneys of the mice were exteriorized and weighed. The appearance and pathological changes of kidneys were recorded, and the kidneys were preserved in 10% neutral formalin for pathological examinations. The pathological score was determined according to the literature, Shackelford et al. Toxicol. Pathol. 30: 93-96, and shown by a score of 0 to 5: a score of 0 represents not present; a score of 1 represents minimal (<1%); a score of 2 represents slight (1-25%); a score of 3 represents moderate (26-50%); a score of 4 represents moderate/severe (51-75%), and a score of 5 represents severe (76-100%).

6.2 Determination of Protein Content in Urine

The abdomen (bladder) of the mouse was gently pressed every 1 to 2 week to make the mouse urinate and the urine was collected in a 1.5 ml centrifuge tube, the protein content (mg/dl) in the urine was determined by urine test strip. The test strip was moistened with the urine and stood for 1 minute, and the protein content was determined by the color shown by the test strip. "−" represents that the urinary protein content is 0 mg/dl; "+/−" represents that the urinary protein content is 10 mg/dl; "+" represents that the urinary protein content is 30 mg/dl; "++" represents that the urinary protein content is 100 mg/dl; "+++" represents that the urinary protein content is 300 mg/dl; "++++" represents that the urinary protein content is 1000 mg/dl. If the color shown by the test strip is between two color regions, the urinary protein content is determined by the mean of the values represented by the two regions.

6.3 Determination of Contents of Blood Urea Nitrogen (BUN) and Creatinine (CRE) in Serum.

0.1 ml blood of the mouse was obtained through tail sampling. After the blood stood at room temperature for 1 to 2 hours, the blood was centrifuged at 6,000 rpm at room temperature for 10 minutes. After that the serum at the upper layer was harvested to determine the contents of blood urea nitrogen (BUN) and creatinine (CRE) in the serum.

The contents of blood urea nitrogen (BUN) and creatinine (CRE) in the serum were determined by FUJI DRI-CHEM 4000i biochemistry analyzer, and the steps are summarized as follows:

Before the experiment, the urea nitrogen and creatinine test strips and the serum to be tested were placed at room temperature to back to room temperature. After that, according to the instructions of the analyzer, 10 μl of serum was added to the central portion of the test strip (if the value exceeded the detectable range, the serum was appropriately diluted with sterilized water), and then determined. After the determination was complete, the contents of blood urea nitrogen (BUN) and creatinine (CRE) in the serum (mg/dl) could be obtained.

7. Method 7: Establishment of Model of Aristolochic Acid (AA)-Induced Nephritis

A drug to be tested (250 mg/kg and 750 mg/kg) was orally administered to female BALB/c mice (LASCO, Taiwan). 3 days later, the BALB/c mice were further administered with 5 mg/kg aristolochic acid through intraperitoneal injection every day. During the administration of aristolochic acid, the mice were still continuously administered drug to be tested (250 mg/kg and 750 mg/kg) and the body weight changes of the mice were recorded. After 12 days of continuous injection of aristolochic acid, the mice were sacrificed, and the serum thereof were sampled for the subsequent serum biochemical value (blood urea nitrogen (BUN) and creatinine (CRE)) analysis. The serum biochemical values were analyzed by a FUJI dry biochemistry analyzer (4000i, FUJI).

8. Method 8: Anti-IL-17 Secretion Drug Screening Through a Platform of EL4 Cells The EL4 cells were seeded into a 96-well plate ($1 \times 10^5$ cells/well), and an appropriate concentration of a drug to be tested was added therein (10 μl/well) and evenly mixed.

Next, the 96-well plate was placed in an incubator at 37° C. with 5% $CO_2$ for 1 hour. After that, the stimuli, phorbol-12-myristate-13-acetate (PMA) (final concentration was 10 ng/ml), and ionomycin (final concentration was 5 ng/ml) were added to the 96-well plate. After being evenly mixed, the 96-well plate was placed in an incubator for 18 hours.

After 18 hours of culturing, the 96-well plate was centrifuged at 1200 rpm for 5 minutes to let the cells precipitate and the supernatant (cell-cultured medium) was transferred to a new 96-well plate (about 155 μl/well).

5 mg/ml of MTT was added into the original 96-well plate (5 μl/well) in which the cells remained, and the original 96-well plate was placed in an incubator at 37° C. with 5% $CO_2$ for 1 hour. After that, DMSO was added to the cells (150 μl/well) to dissolve out the crystal violet. After the liquids in the 96-well plate were evenly mixed, the absorbance at 570 nm of each well was measured and the cell viability was further calculated.

The cell-cultured medium in the new 96-well plate was 2-4 fold diluted and the IL-17 concentration was determined by mouse IL-17 ELISA kit (R&D, DY421E).

For both of cell viability and IL-17 content assays, the results of the group with phorbol-12-myristate-13-acetate (PMA) and ionomycin were set as 100%, and the secretion of IL-17 was expressed by percentage.

B. Results (A) Effects of Ethanol Extract of *Clausena lansium*

Ethanol extract of *Clausena lansium* was obtained through Method 1 mentioned above, and named HE-07.

1. Effects of the Ethanol Extract of *Clausena lansium* HE-07 on Peripheral Blood Leukocytes (PBLs) and Th17 Cells Effects of the ethanol extract of *Clausena lansium* HE-07 on cell viability and on IL-17 secretion of peripheral blood leukocytes (PBLs) of rats and Th17 cells differentiated from CD4+ T cells were determined through Method 2 and Method 3 mentioned above, respectively. The results are shown in Table 1 and Table 2, respectively.

TABLE 1

Effects of the ethanol extract of *Clausena lansium* HE-07 on cell viability and IL-17 secretion of peripheral blood leukocytes (PBLs) of rats

| Drug to be tested | Test in peripheral blood leukocyte (PBL) | Concentration | | |
|---|---|---|---|---|
| | | 1.9 μg/ml | 7.5 μg/ml | 30 μg/ml |
| HE-07 | IL-17 inhibition (%) | 20.1 ± 5.8 | 43.3 ± 10.1 | 79.5 ± 6.6 |
| | Cell viability (%) | 108.4 ± 7.9 | 99.7 ± 8.1 | 103.3 ± 2.1 |

TABLE 2

Effects of the ethanol extract of *Clausena lansium* HE-07 on cell viability and IL-17 secretion of Th17 cells differentiated from CD4+ T cells

| Drug to be tested | Test for Th17 cells | Concentration | |
|---|---|---|---|
| | | 12.5 μg/ml | 25 μg/ml |
| HE-07 | IL-17 inhibition (%) | 0.8 ± 0.4 | 65.2 ± 0.5 |
| | Cell viability (%) | 101.5 ± 3.9 | 86.4 ± 0.9 |

The results in Table 1 and Table 2 show that the ethanol extract of *Clausena lansium* HE-07 effectively inhibits IL-17 secretion in two types of cells.

Currently, it is known that IL-17 plays a key role in autoimmune diseases, such as psoriasis, psoriatic arthritis, ankylosing spondylitis, etc., and it has been clinically proven that a monoclonal antibody of IL-17 has a significant effect in treating the above-mentioned autoimmune diseases, and the results of animal studies and clinical data show that IL-17 is associated with lupus erythematosus. Therefore, the ethanol extract of *Clausena lansium* with the inhibitory effect on IL-17 secretion could be applied to the treatment of the above-mentioned autoimmune diseases.

2. Effects of the Ethanol Extract of *Clausena lansium* HE-07 on CXCL9 Production in IFN-γ Treated Monocytes CXCL9 is a lupus erythematosus-related chemokine. Effects of the ethanol extract of *Clausena lansium* HE-07 on CXCL9 production in IFN-γ treated monocytes were determined by Method 4 mentioned above. The results are shown in Table 3.

TABLE 3

Effects of the ethanol extract of *Clausena lansium* HE-07 on CXCL9 production in IFN-γ treated monocytes

| Drug to be tested | Test | $IC_{50}$ (μg/ml) |
|---|---|---|
| HE-07 | CXCL9 inhibition | <3.125 |
| | Cytotoxicity | >50 |

The results show that the ethanol extract of *Clausena lansium* HE-07 can effectively inhibit CXCL9 secretion in IFN-γ treated monocytes.

3. Effects of the ethanol extract of *Clausena lansium* HE-07 on production of the inflammatory factors, TNF-α and IL-6, in the model of lipopolysaccharide (LPS)-induced acute inflammation in mice TNF-α and IL-6 are generally recognized and accepted factors related to inflammation. Effects of the ethanol extract of *Clausena lansium* HE-07 on production of the inflammatory factors, TNF-α and IL-6, in the model of lipopolysaccharide (LPS)-induced acute inflammation in mice were determined through Method 5 mentioned above. The results are shown in FIG. 1A and FIG. 1B.

Figure 1B:
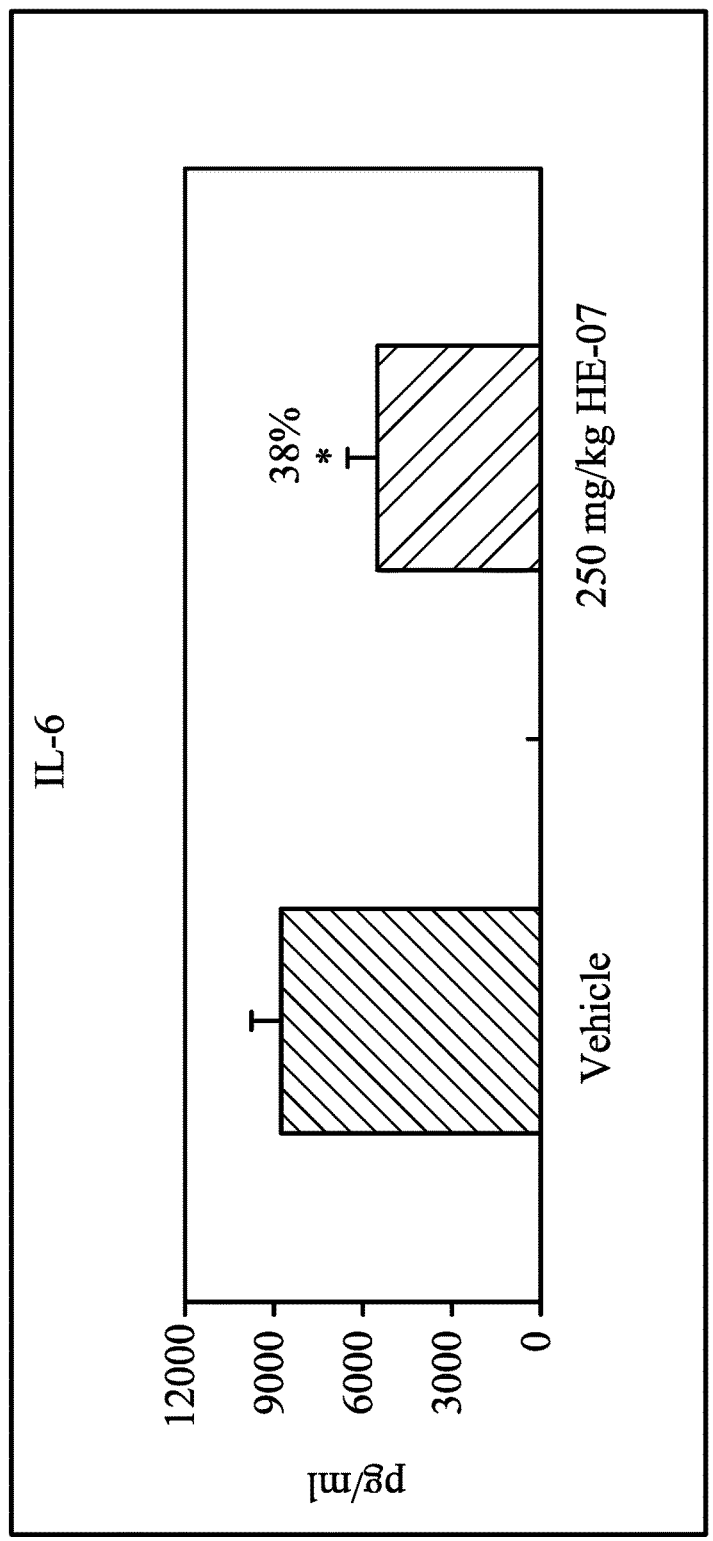
FIG. 1B shows the effects of the ethanol extract of *Clausena lansium* (HE-07) on production of the inflammatory factor, IL-6, in the model of lipopolysaccharide (LPS)-induced acute inflammation in mice.

According to the results shown in FIG. 1A and FIG. 1B, the ethanol extract of *Clausena lansium* HE-07 inhibit TNF-α and IL-6 production significantly in lipopolysaccharide (LPS)-induced acute inflammation in mice.

Since the ethanol extract of *Clausena lansium* has a significant inhibitory effect on TNF-α or IL-6 production and it is also known that TNF-α or IL-6 is involved in autoimmune diseases, therefore the ethanol extract of *Clausena lansium* could be applied to the treatment or alleviation of autoimmune diseases, such as rheumatoid arthritis, juvenile idiopathic arthritis, Crohn's disease, ulcerative colitis (UC), etc.

4. Effects of the Ethanol Extract of *Clausena lansium* (HE-07) on NZBWF1/J Mice NZBWF1/J mouse is a commonly used autoimmune animal model of systemic lupus erythematosus (SLE). Effects of the ethanol extract of *Clausena lansium* (HE-07) on NZBWF1/J mice were determined through Method 6 mentioned above. The results are shown in FIGS. 2A to 2F and Table 4.

TABLE 4

Effects of the ethanol extract of *Clausena lansium* (HE-07) on the survival rate of NZBWF1/J mice

| Drug to be tested | Survival rate (%) | Statistical analysis |
|---|---|---|
| Vehicle: | 40 | |
| 300 mg/kg HE-07 | 90 | 0.0289* |
| 50 mg/kg cyclophosphamide (CTX) (Drug for clinical treatment for lupus erythematosus) | 100 | 0.004* |

Kaplan-Meier method

Figure 2A:
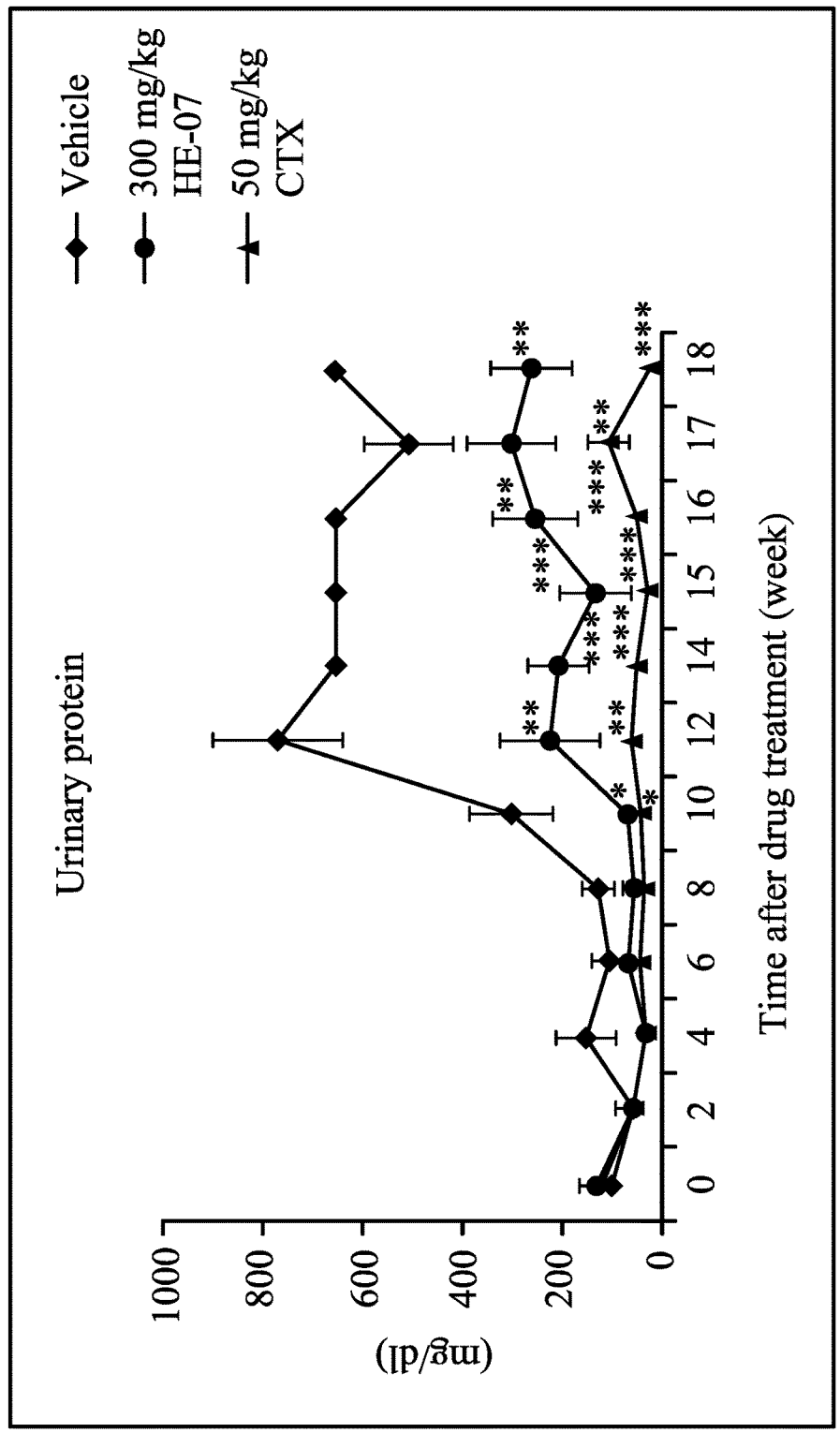
FIG. 2A shows the effects of the ethanol extract of *Clausena lansium* (HE-07) on the protein content in the urine of the NZBWF1/J mice.
Figure 2B:
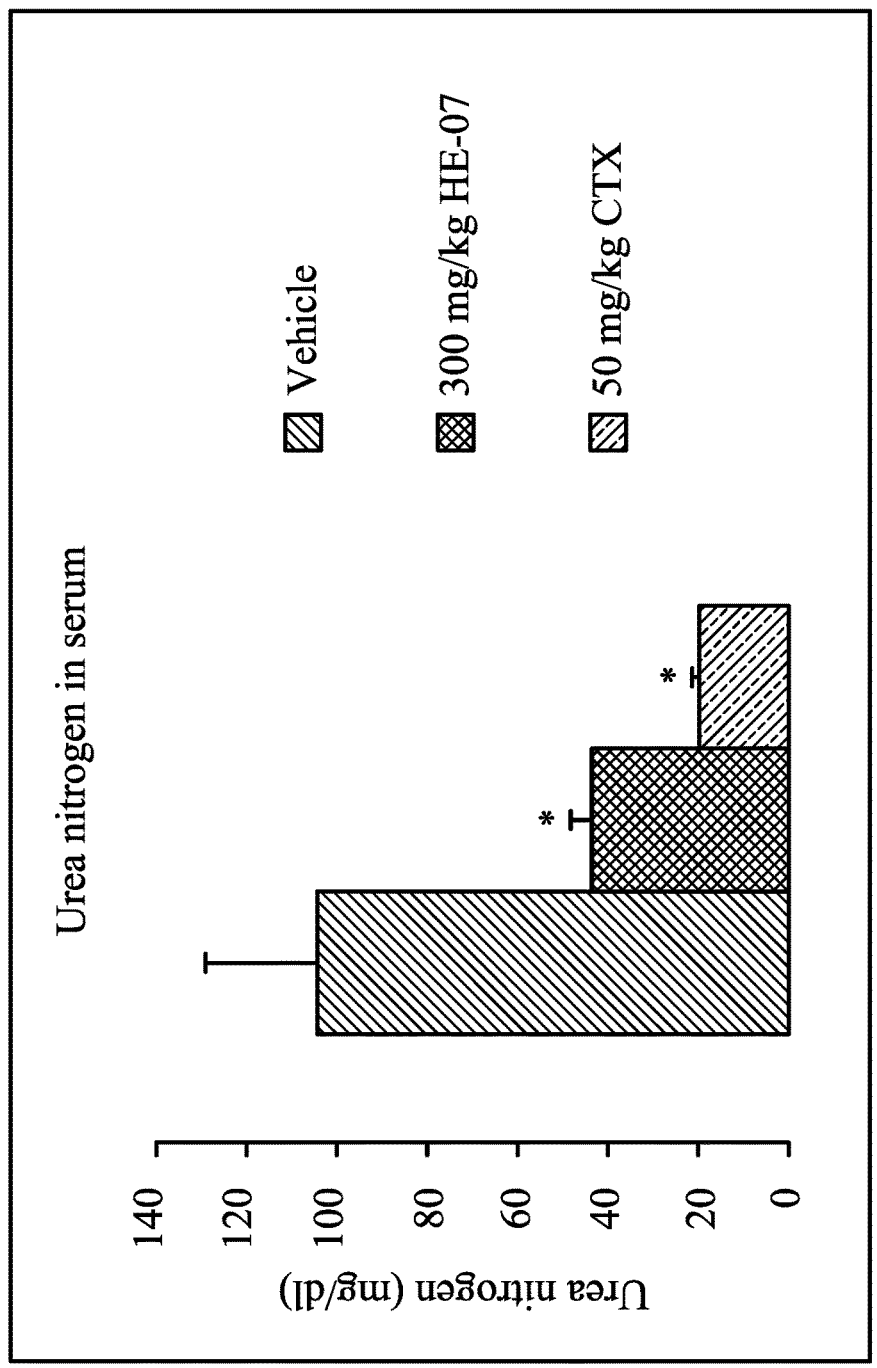
FIG. 2B shows the effects of the ethanol extract of *Clausena lansium* (HE-07) on the content of blood urea nitrogen in the serum of NZBWF1/J mice.
Figure 2C:
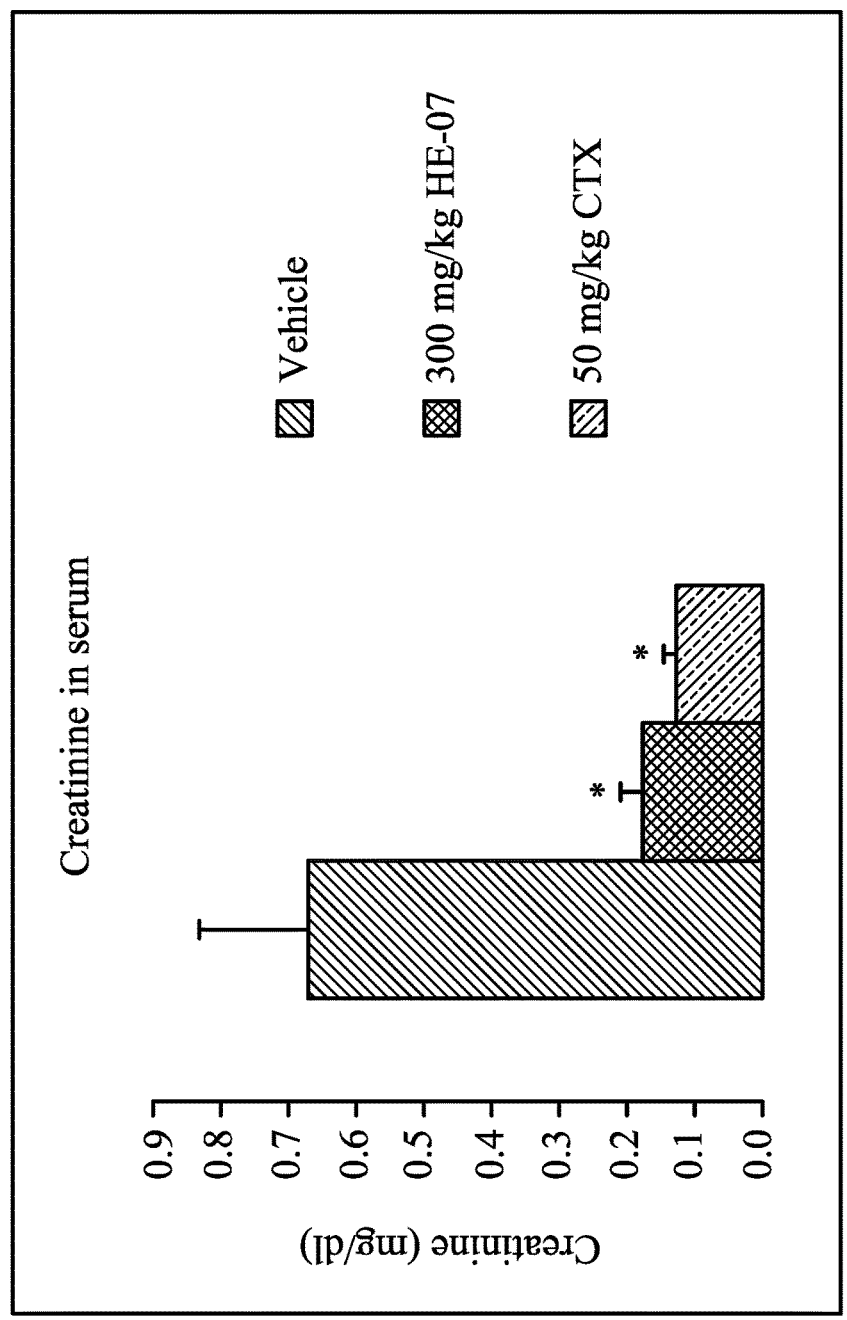
FIG. 2C shows the effects of the ethanol extract of *Clausena lansium* (HE-07) on the content of creatinine in the serum of NZBWF1/J mice.

FIG. 2A shows that the ethanol extract of *Clausena lansium* HE-07 effectively reduces protein content in the urine of the NZBWF1/J mice. Moreover, based on the results shown in FIG. 2B and FIG. 2C, the ethanol extract of *Clausena lansium* HE-07 reduces the contents of urea nitrogen and creatinine in the serum of NZBWF1/J mice significantly as well.

Figure 2D:
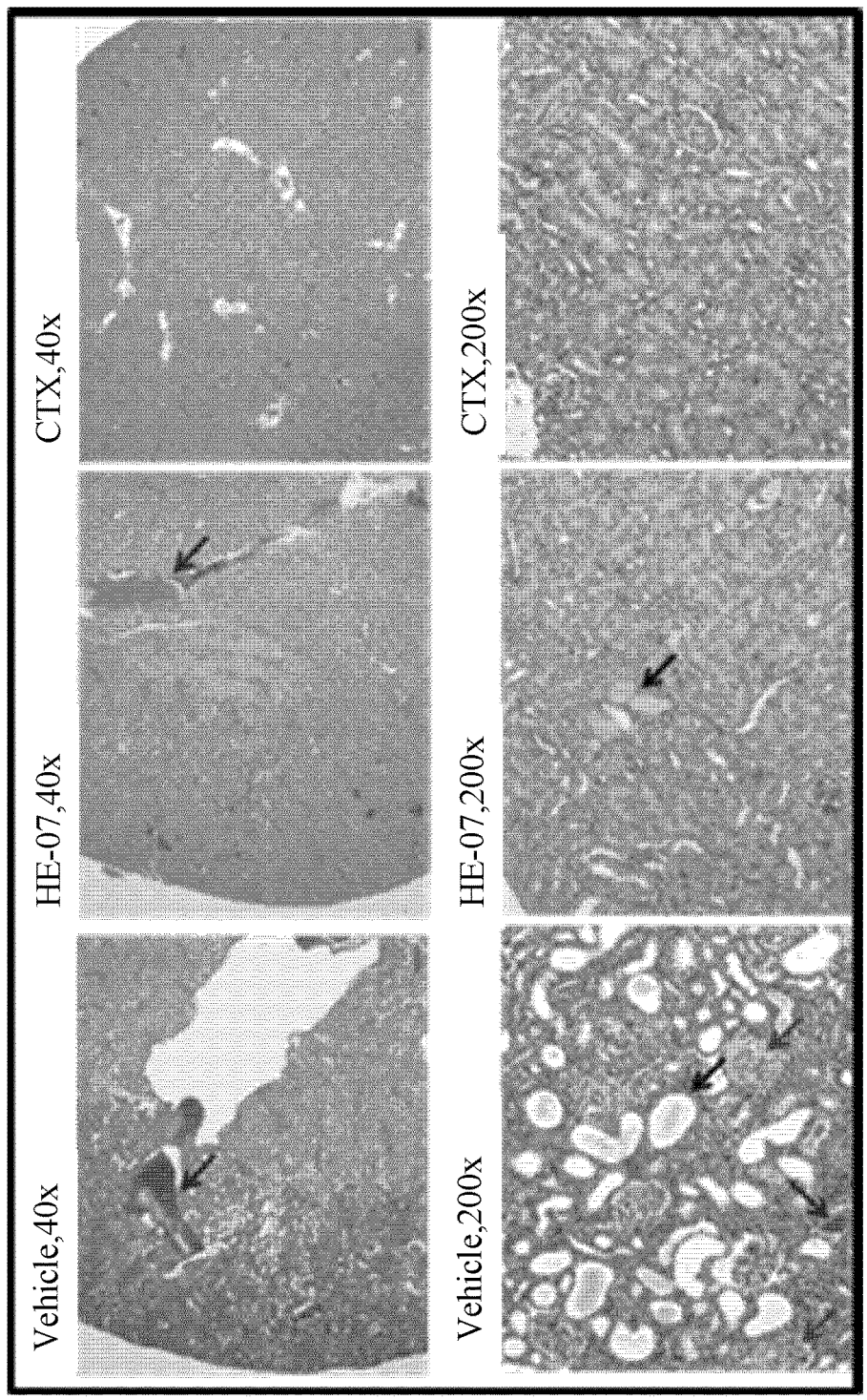
FIG. 2D shows pathological staining results for kidney tissues of NZBWF mice treated with vehicle, the ethanol extract of *Clausena lansium* (HE-07) and cyclophosphamide (CTX).
Figure 2E:
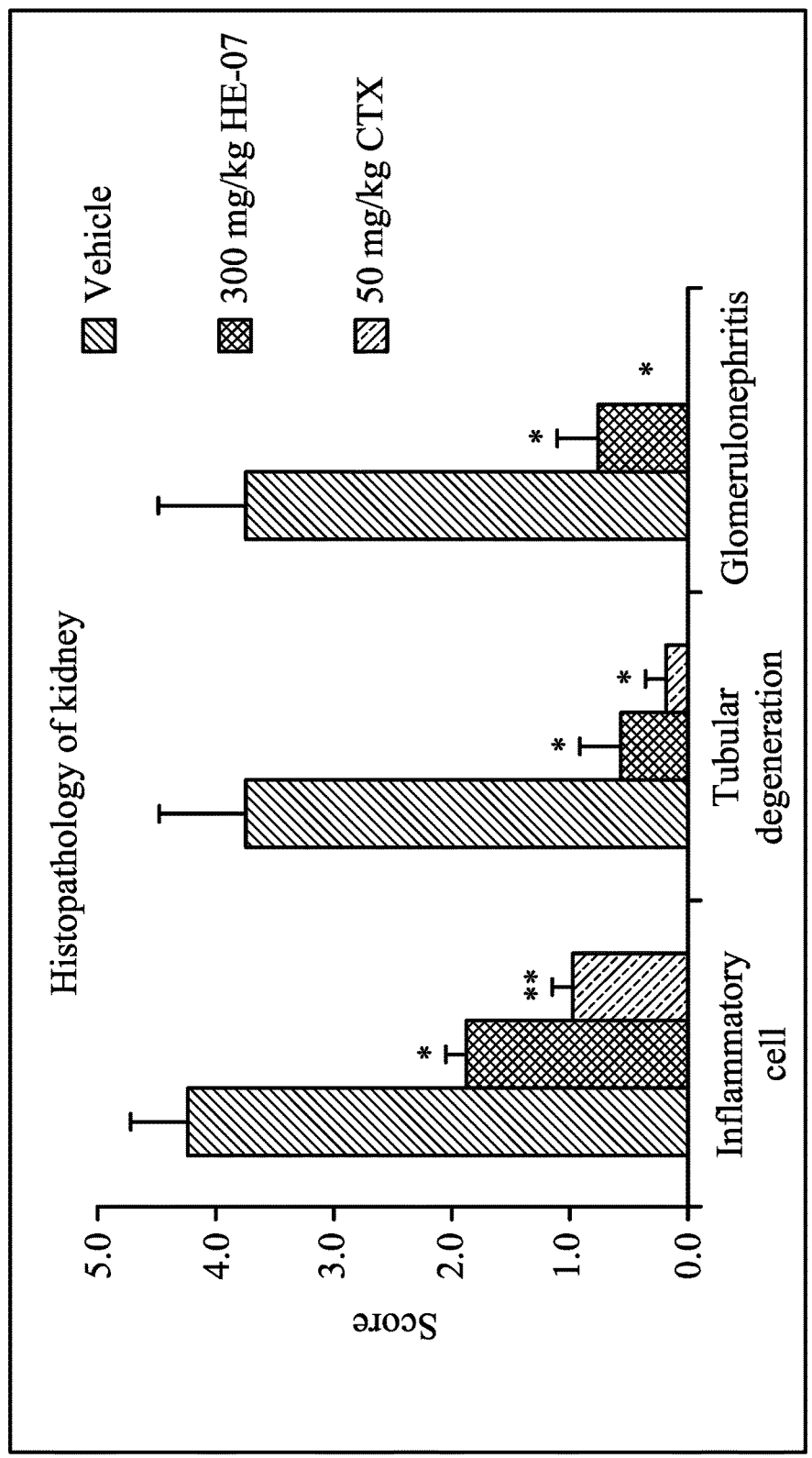
FIG. 2E shows the effects of the ethanol extract of *Clausena lansium* (HE-07) on kidney inflammation, tubular degeneration and glomerulonephritis of NZBWF1/J mice.

Furthermore, according to FIG. 2D and FIG. 2E, the infiltration of inflammatory cells, the tubular degeneration and glomerulonephritis are all reduced significantly in NZBWF1/J mice treated with the ethanol extract of *Clausena lansium* HE-07.

Figure 2F:
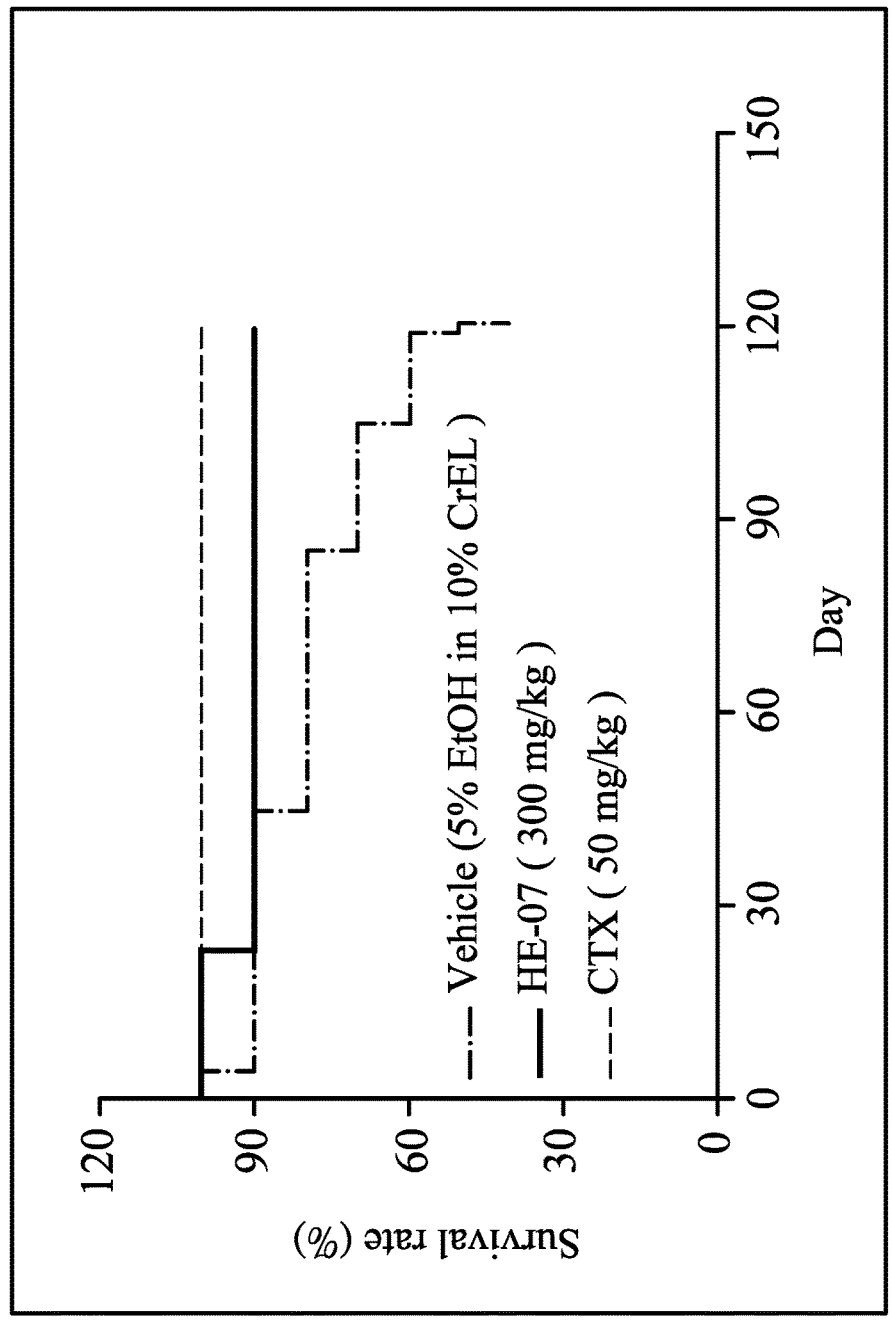
FIG. 2F shows the effects of the ethanol extract of *Clausena lansium* (HE-07) on the survival rate of NZBWF1/J mice. Survival analysis was performed by Kaplan-Meier method and GraphPad Prism 6 software, and each group was compared with the vehicle group, and the results show that the 300 mg/kg HE-07 group and the vehicle group have significant differences ($p<0.05$), and the 50 mg/kg CTX group and the vehicle group also have significant differences ($p<0.01$).

In addition, FIG. 2F and Table 4 show that the ethanol extract of *Clausena lansium* (HE-07) is capable of significantly increasing the survival rate of NZBWF1/J mice.

Since the ethanol extract of *Clausena lansium* effectively alleviated nephritis and increased the survival rate of NZBWF1/J mice that is commonly used as the lupus erythematosus animal model, it could be applied the ethanol extract of *Clausena lansium* to the treatment of lupus erythematosus and lupus nephritis.

5. Effects of the Ethanol Extract of *Clausena lansium* HE-07 on Mice with Aristolochic Acid (AA)-Induced Nephritis Effects of the ethanol extract of *Clausena lansium* HE-07 on the body weights, contents of blood urea nitrogen (BUN) in serum and creatinine (CRE) in serum of mice with aristolochic acid-induced nephritis were determined by Method 7 mentioned above. The results are shown in FIGS. 3A and 3B, FIGS. 4A and 4B, and FIGS. 5A and 5B, respectively.

Figure 3A:
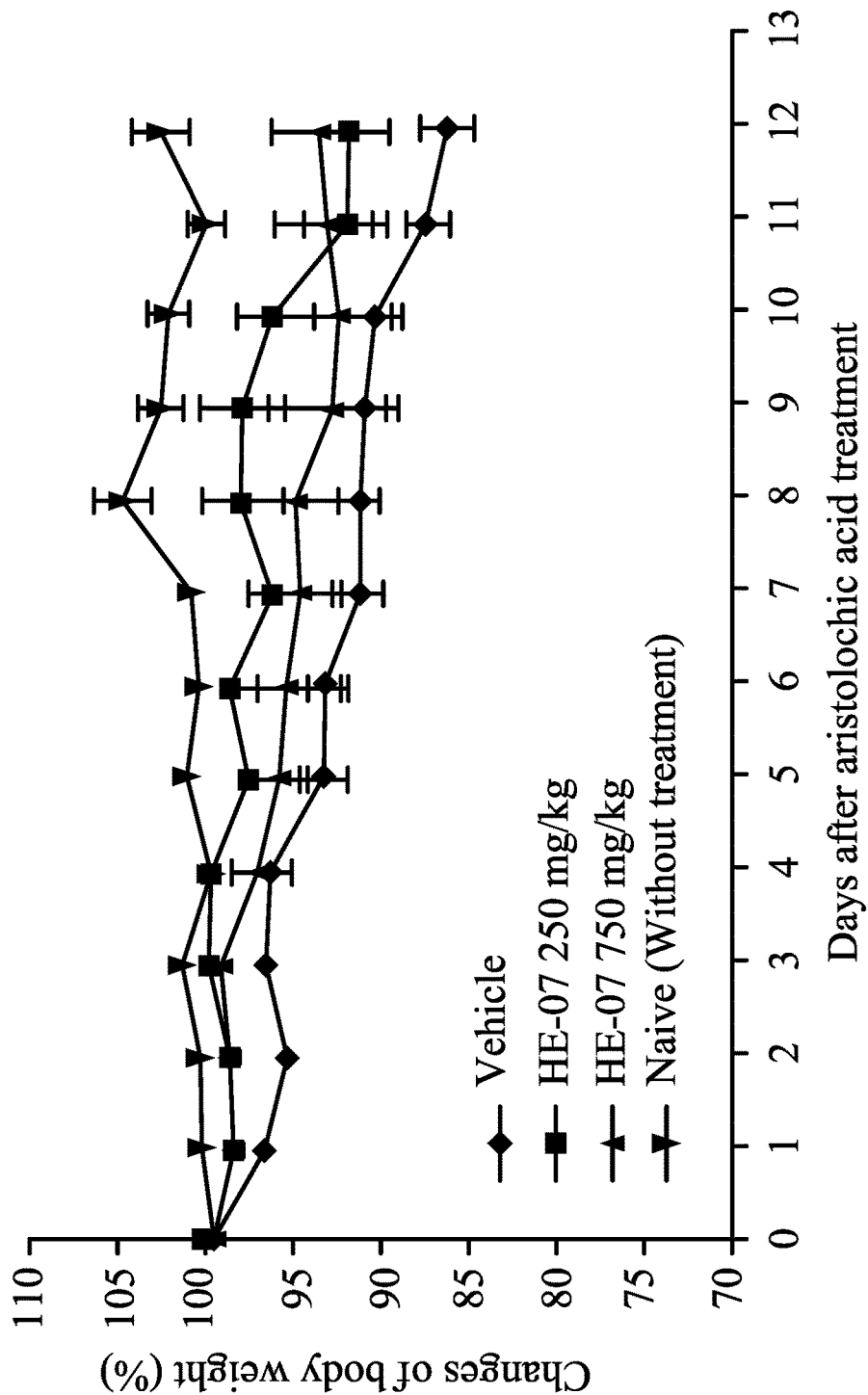
FIG. 3A shows the effects of the ethanol extract of *Clausena lansium* (HE-07) on body weight changes of mice with aristolochic acid (AA)-induced nephritis.
Figure 3B:
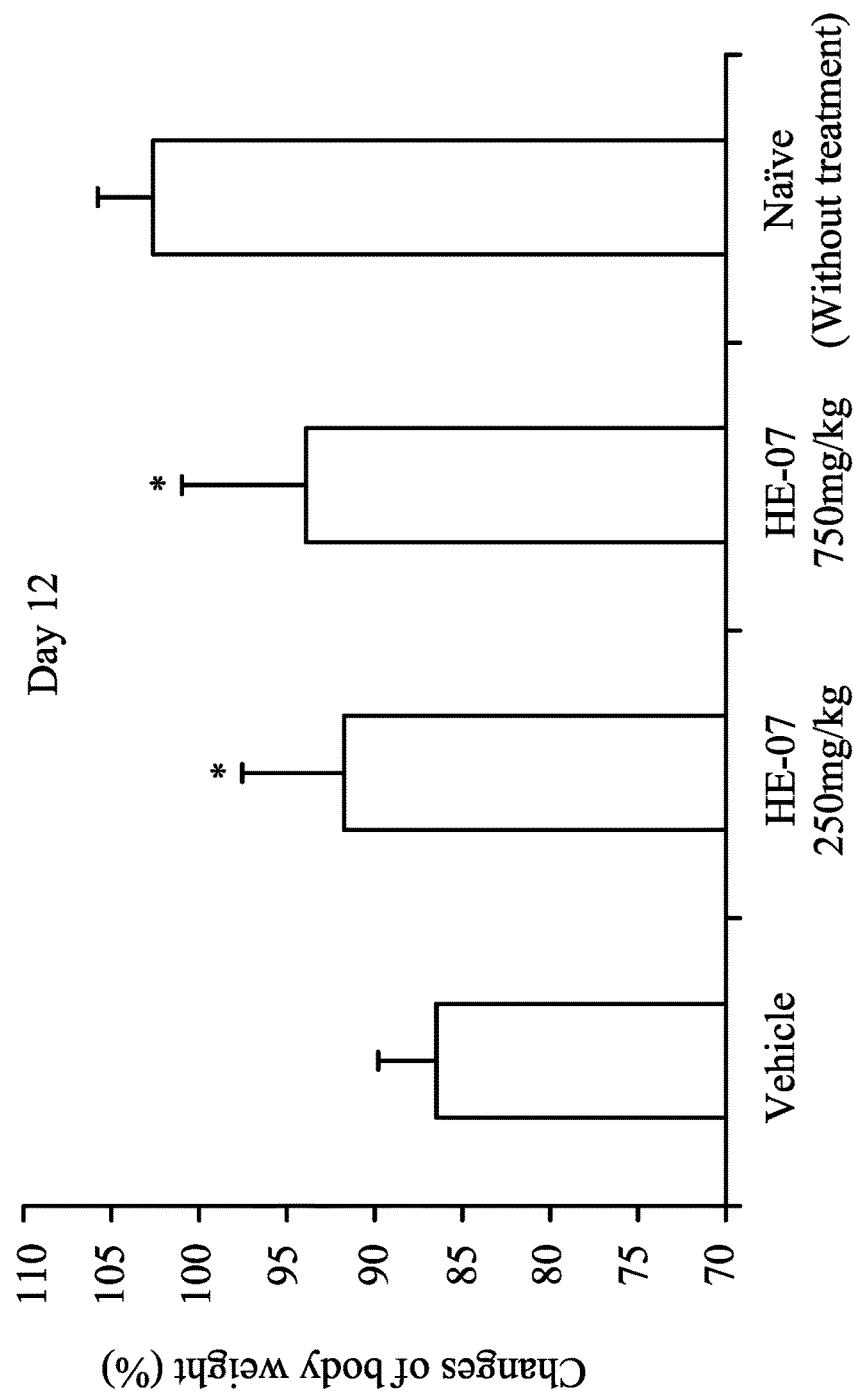
FIG. 3B shows the body weight changes of mice treated with the vehicle, treated with the ethanol extract of *Clausena lansium* (HE-07), and without treatment on day 12 after administration of aristolochic acid. There is significant difference when compared with the vehicle treatment group: *$p<0.05$.

FIGS. 3A and 3B show that 12 days after inducing nephritis in the mice using aristolochic acid, the ethanol extract of *Clausena lansium* HE-07 has an effect of alleviating the decrease of body weights of the mice.

Figure 4A:
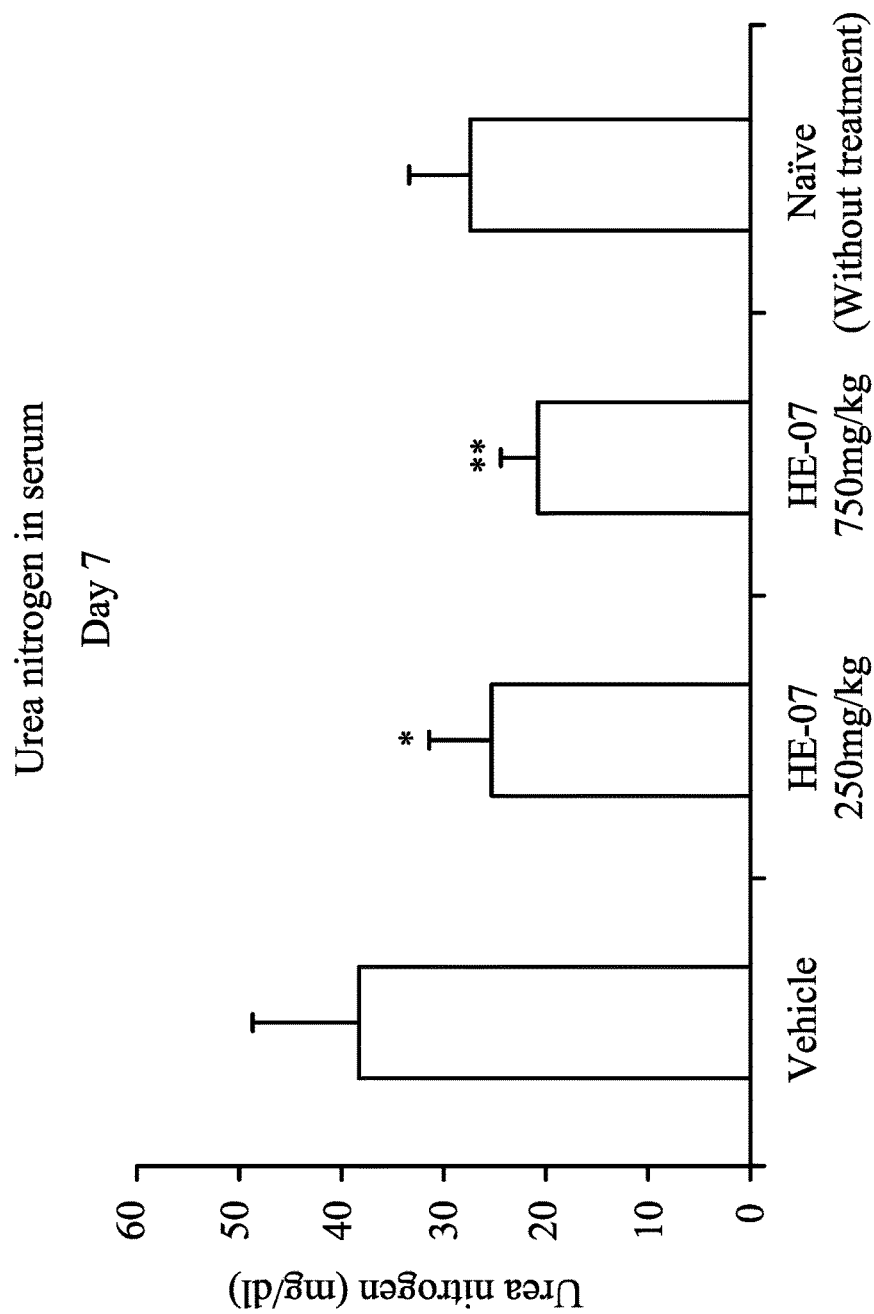
FIG. 4A shows the content of blood urea nitrogen (BUN) in serum of mice treated with the vehicle, treated with the ethanol extract of *Clausena lansium* (HE-07), and without treatment on day 7 after administration of aristolochic acid. There is significant difference when compared with the vehicle treatment group: *$p<0.05$; **$p<0.01$.
Figure 4B:
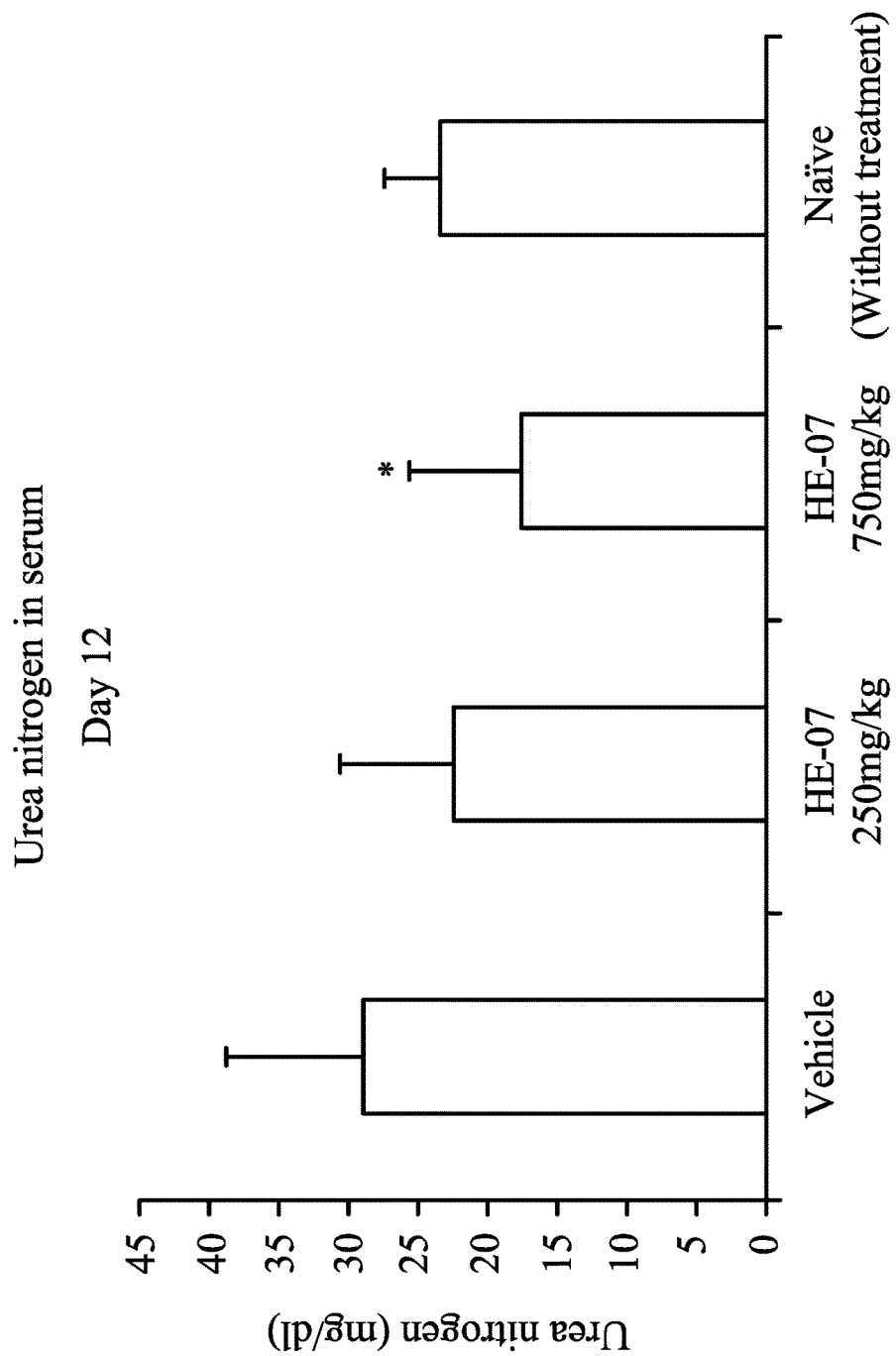
FIG. 4B shows the content of blood urea nitrogen (BUN) in serum of mice treated with the vehicle, treated with the ethanol extract of *Clausena lansium* (HE-07), and without treatment on day 12 after administration of aristolochic acid. There is significant difference when compared with the vehicle treatment group: *$p<0.05$.

According to FIGS. 4A and 4B, it is clearly known that after inducing nephritis in the mice using aristolochic acid, the ethanol extract of *Clausena lansium* HE-07 significantly decreases the content of blood urea nitrogen (BUN) in the serum of the mice.

Figure 5A:
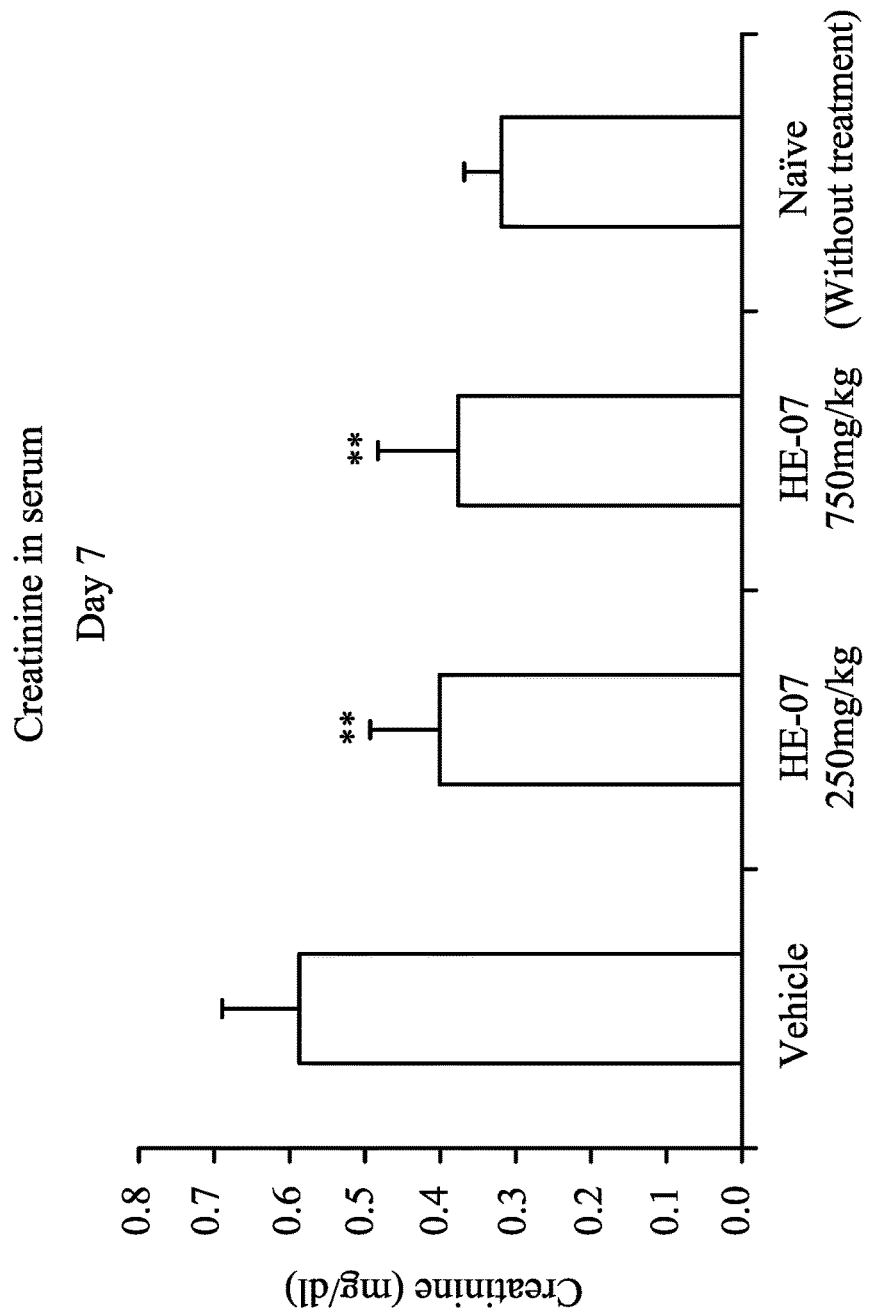
FIG. 5A shows the content of creatinine (CRE) in serum of mice treated with the vehicle, treated with the ethanol extract of *Clausena lansium* (HE-07), and without treatment on day 7 after administration of aristolochic acid. There is significant difference when compared with the vehicle treatment group: **p<0.01.
Figure 5B:
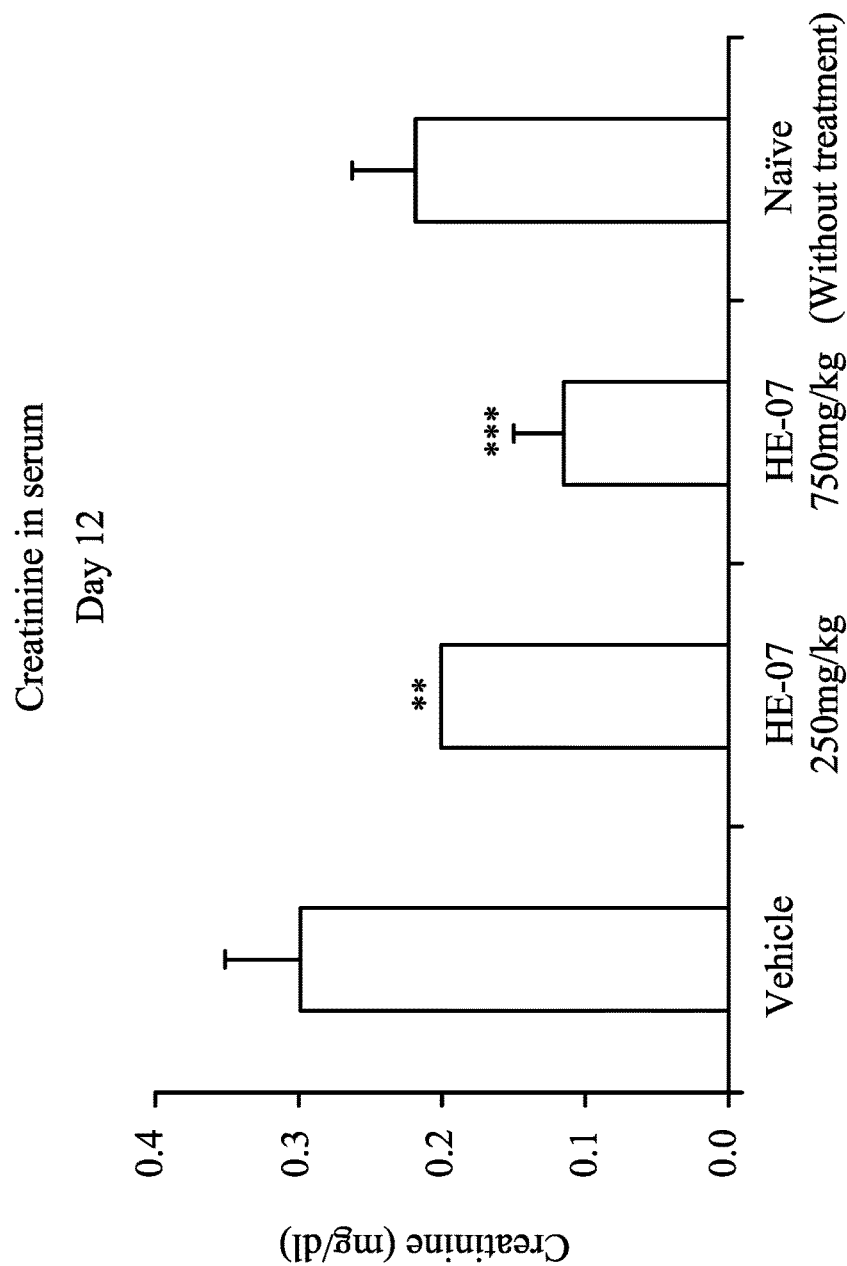
FIG. 5B shows the content of creatinine (CRE) in serum of mice treated with the vehicle, treated with the ethanol extract of *Clausena lansium* (HE-07), and without treatment on day 12 after administration of aristolochic acid. There is significant difference when compared with the vehicle treatment group: p<0.01; *p<0.001

Moreover, FIGS. 5A and 5B show that, after inducing nephritis in the mice using aristolochic acid, the ethanol extract of *Clausena lansium* HE-07 significantly decreases the content of creatinine (CRE) in the serum of the mice.

Based on the results mentioned above, it is known that the ethanol extract of *Clausena lansium* is effectively capable of alleviating aristolochic acid-induced nephritis, and could be applied to the treatment related to nephritis.

(B) Effect of active fraction from ethanol extract of *Clausena lansium*

1. Determination of Active Fraction from the Ethanol Extract of *Clausena lansium* HE-07

The ethanol extract of *Clausena lansium* HE-07 was analyzed through high-performance liquid chromatography and thin layer chromatography, and respective fractions of the ethanol extract of *Clausena lansium* HE-07 were obtained and activity test was performed thereon to determine the active fraction of the ethanol extract of *Clausena lansium* HE-07, and then the active fraction was named HE-07-X.

After that the active fraction HE-07-X was analyzed by nuclear magnetic resonance spectroscopy (NMR spectroscopy), 6 compounds were determined in HE-07-X, and they are numbered as F8m, F7m, F6m, F5m, F4m and F3m, respectively.

Figure 6:
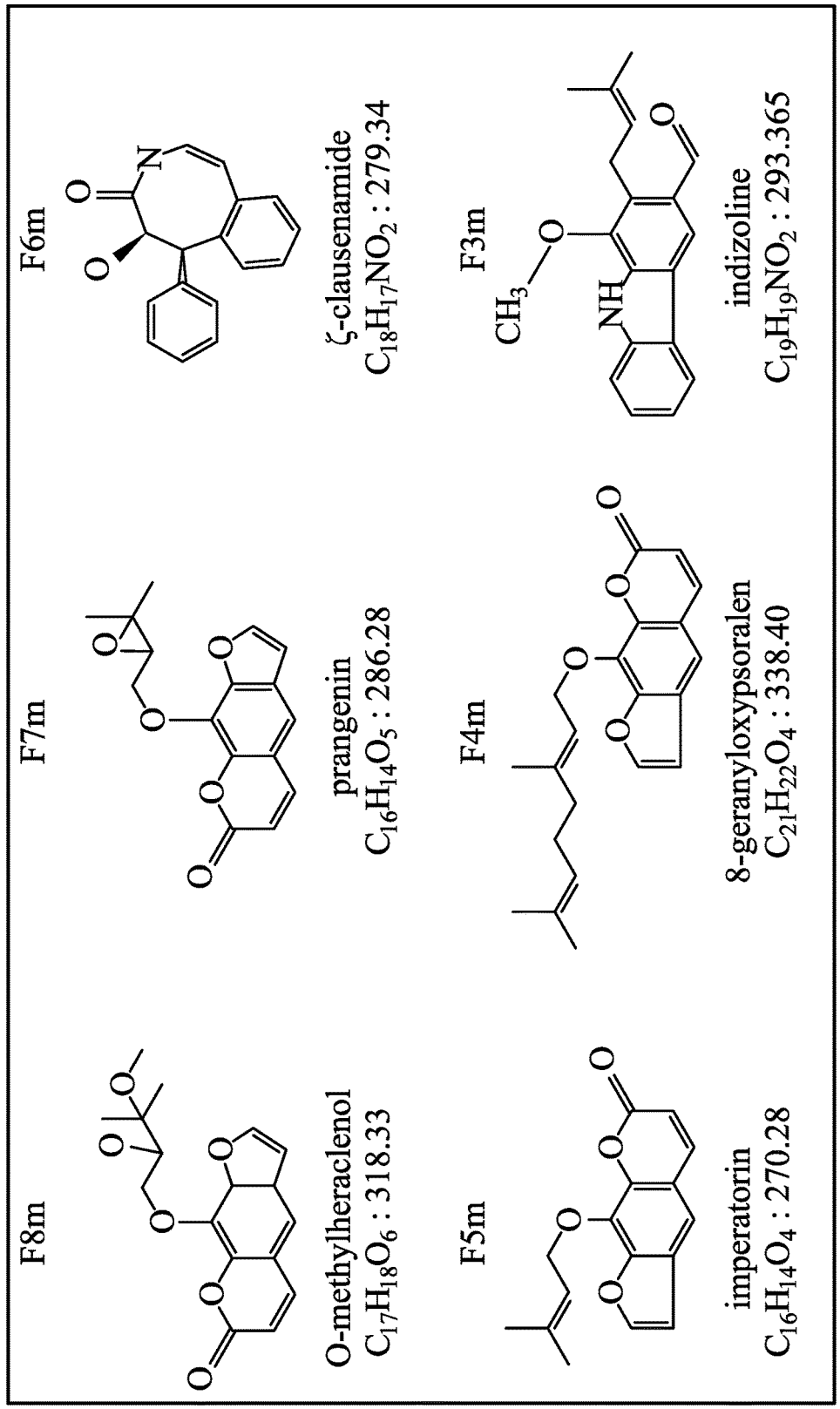
FIG. 6 shows the structures of the 6 compounds in the active fraction HE-07-X from the ethanol extract of *Clausena lansium*.

The structures of F8m, F7m, F6m, F5m, F4m and F3m are shown in FIG. 6., wherein F8m is O-methylheraclenol (O-methylheraclenol), F7m is prangenin, F6m is ζ-clausenamide, F5m is imperatorin, F4m is 8-geranyloxypsoralen, and F3m is indizoline.

Furthermore, the contents of the above-mentioned 6 compounds in the active fraction HE-07-X are shown in Table 5.

TABLE 5

Contents of the 6 compounds in the active fraction HE-07-X

| F8m (wt %) | F7m (wt %) | F6m (wt %) | F5m (wt %) | F4m (wt %) | F3m (wt %) | Total amount (wt %) |
|---|---|---|---|---|---|---|
| 1.30 | 4.44 | 1.47 | 29.38 | 18.89 | 0.63 | 56.11 |

According to Table 5, it is known that compounds, F8m, F7m, F6m, F5m, F4m and F3m totally occupy 56.11 wt % of the active fraction HE-07-X.

2. Effects of the Active Fraction HE-07-X on IL-17 Secretion in Peripheral Blood Leukocytes (PBLs) of Rats and EL4 Cells Effects of the active fraction HE-07-X on IL-17 secretion in peripheral blood leukocytes (PBLs) and EL4 cells were determined through Method 2 and Method 8 mentioned above, respectively. The results are shown in Table 6.

TABLE 6

Effects of the active fraction HE-07-X on IL-17 secretion in peripheral blood leukocytes (PBLs) and EL4 cells

| | $IC_{50}$ (μg/ml) | |
|---|---|---|
| Drug to be tested | Peripheral blood leukocyte (PBL) IL-17 inhibition | EL4 cells IL-17 inhibition |
| HE-07-X | 5.6 | 10.4 ± 4.4 |

According to Table 6, it is known that the active fraction HE-07-X from the ethanol extract of *Clausena lansium* is capable of inhibiting peripheral blood leukocyte (PBL) and EL4 cells secreting IL-17.

The active fraction HE-07-X from the ethanol extract of *Clausena lansium* is capable of inhibiting IL-17 secretion, and it has been clinically proven that a monoclonal antibody of IL-17 has a significant effect in treating the above-mentioned autoimmune diseases, and the animal experiments and clinical data show that IL-17 is associated with lupus erythematosus. Therefore, the active fraction HE-07-X from the ethanol extract of *Clausena lansium* could be applied to the treatment of autoimmune disease, such as psoriasis, psoriatic arthritis, ankylosing spondylitis, lupus erythematosus, lupus nephritis, etc.

3. Effects of the Active Fraction HE-07-X on CXCL9 Production in IFN-γ Treated Monocytes Effects of the active fraction HE-07-X on CXCL9 production in IFN-γ treated monocytes were determined by Method 4 mentioned above. The results are shown in Table 7.

TABLE 7

Effects of the active fraction HE-07-X on CXCL9 produced in IFN-γ treated monocytes

| Drug to be tested | $IC_{50}$ (μg/ml) THP-1 cells CXCL9 inhibition |
|---|---|
| HE-07-X | 30.7 ± 3.5 |

According to Table 7, it is known that the active fragment of the ethanol extract of Clausena lansium HE-07-X is capable of inhibiting THP-1 cells secreting CXCL9.

4. Effects of the Active Fraction HE-07-X on Production of the Inflammatory Factors, TNF-α and MCP-1, in the Model of Lipopolysaccharide-Induced Acute Inflammation in Mice TNF-α and MCP-1 are generally recognized and accepted factors related to inflammation. Effects of the active fraction HE-07-X on production of the inflammatory factors, TNF-α and MCP-1, in the model of lipopolysaccharide-induced acute inflammation in mice were determined by Method 5 mentioned above. The results are shown in FIG. 7A and FIG. 7B.

Figure 7A:
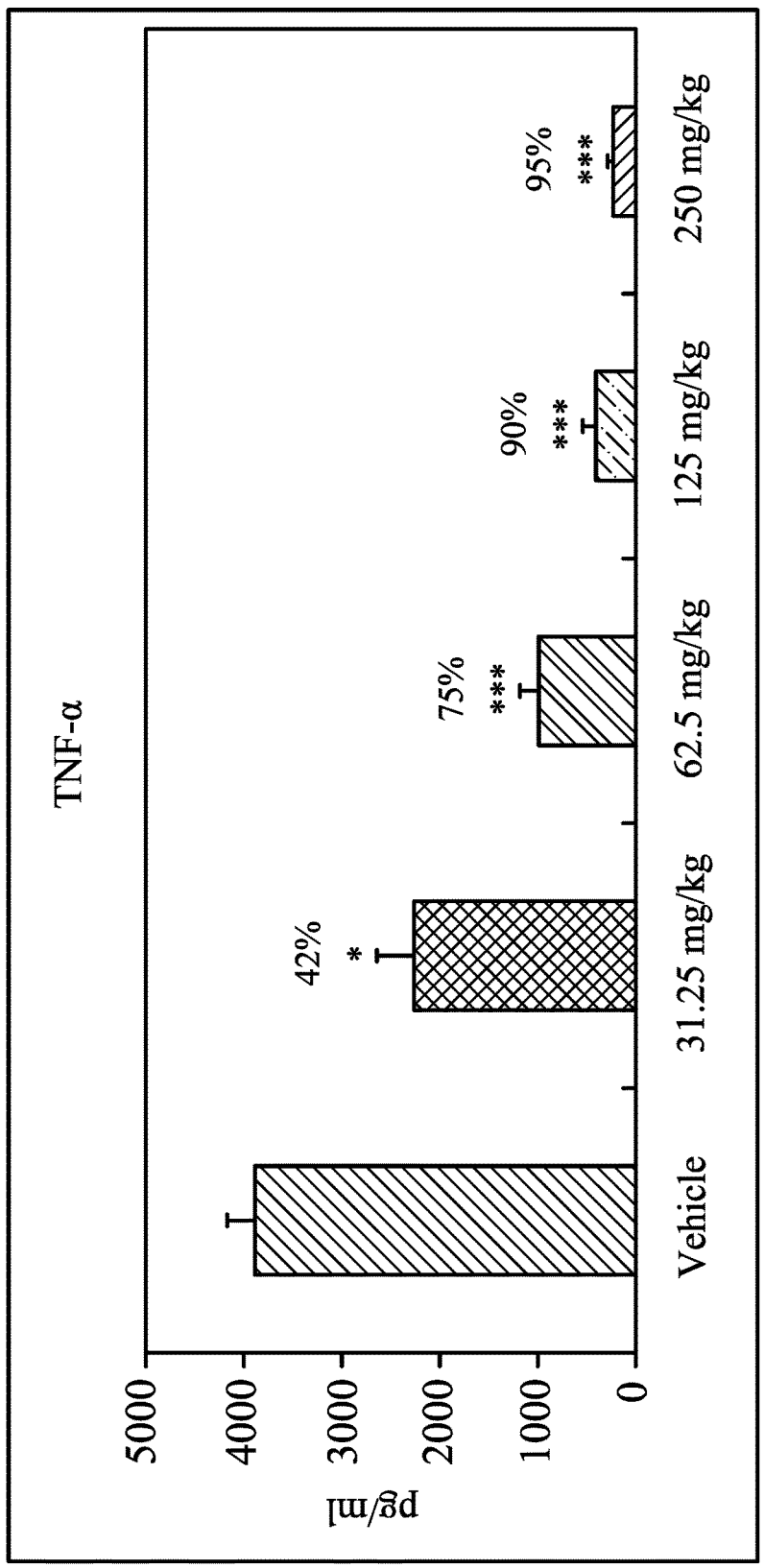
FIG. 7A shows the effects of the active fraction HE-07-X from the ethanol extract of *Clausena lansium* on production of the inflammatory factors, TNF-α, in the model of lipopolysaccharide-induced acute inflammation in mice.
Figure 7B:
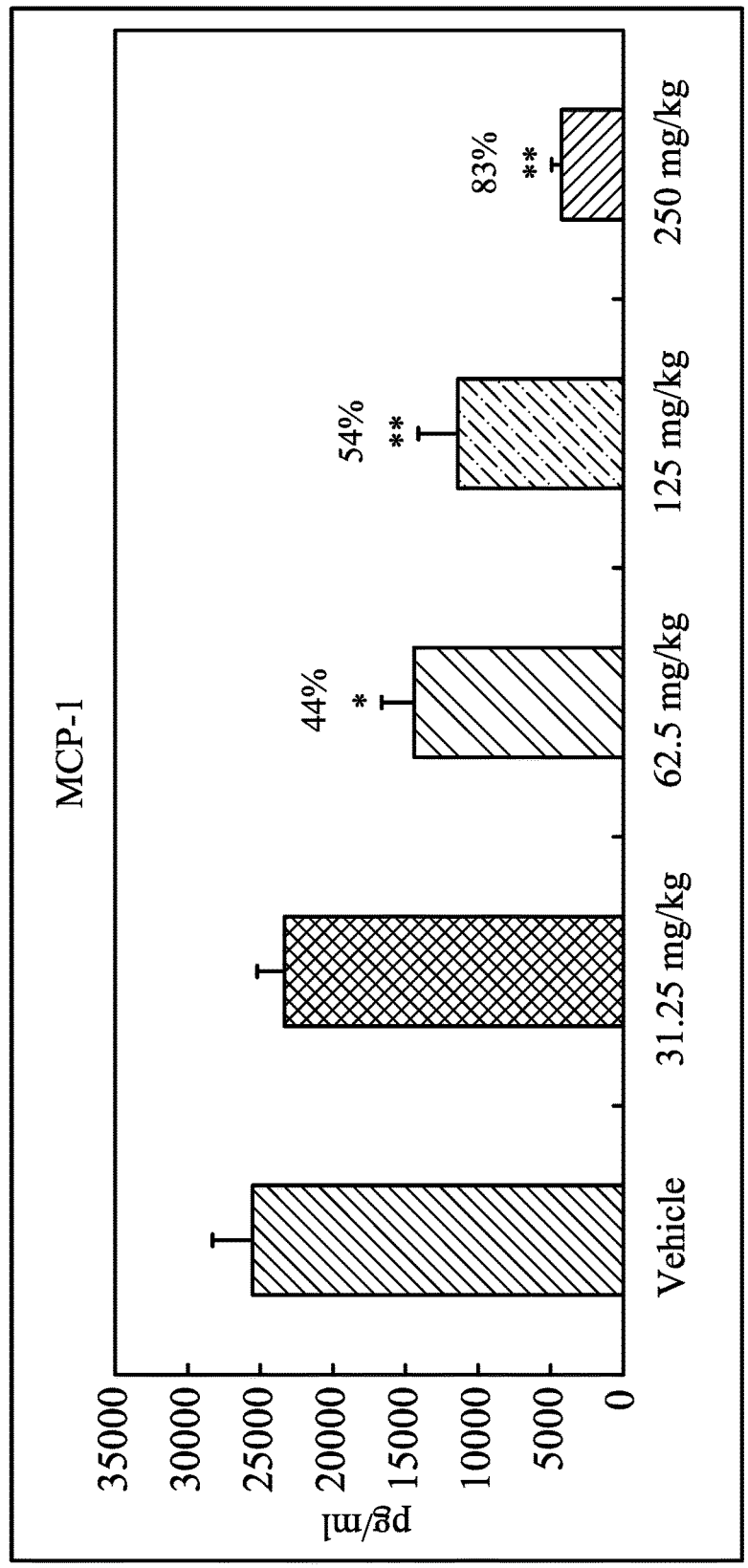
FIG. 7B shows the effects of the active fraction HE-07-X from the ethanol extract of *Clausena lansium* on production of the inflammatory factor, MCP-1, in the model of lipopolysaccharide-induced acute inflammation in mice.

According to FIG. 7A and FIG. 7B, the active fraction HE-07-X can significantly inhibit the production of the inflammatory factors TNF-α and MCP-1 in a dose dependent manner in lipopolysaccharide-induced acute inflammation in mice.

Since the TNF-α or MCP-1 is involved in autoimmune diseases, and the active fraction HE-07-X can significantly inhibit the production of them, the active fraction HE-07-X could be applied to treatment or alleviation of autoimmune disease, such as rheumatoid arthritis, juvenile idiopathic arthritis, Crohn's disease, ulcerative colitis (UC), lupus erythematosus, lupus nephritis, etc.

5. Effects of the Active Fraction HE-07-X on NZBWF1/J Mice

Figure 8A:
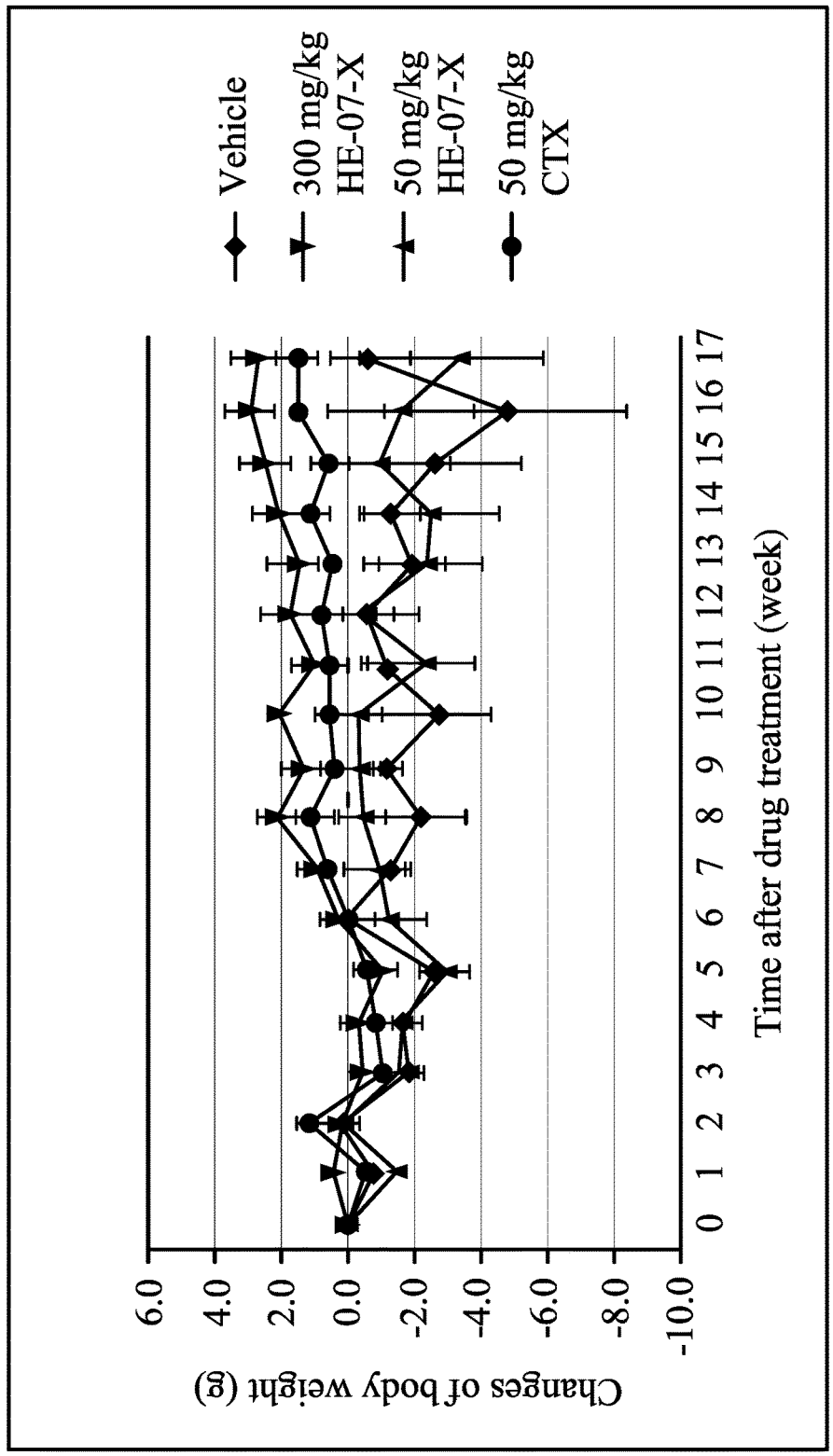
FIG. 8A shows the effects of the active fraction HE-07-X from the ethanol extract of *Clausena lansium* on body weights of mice in the animal model of lupus erythematosus.
Figure 8B:
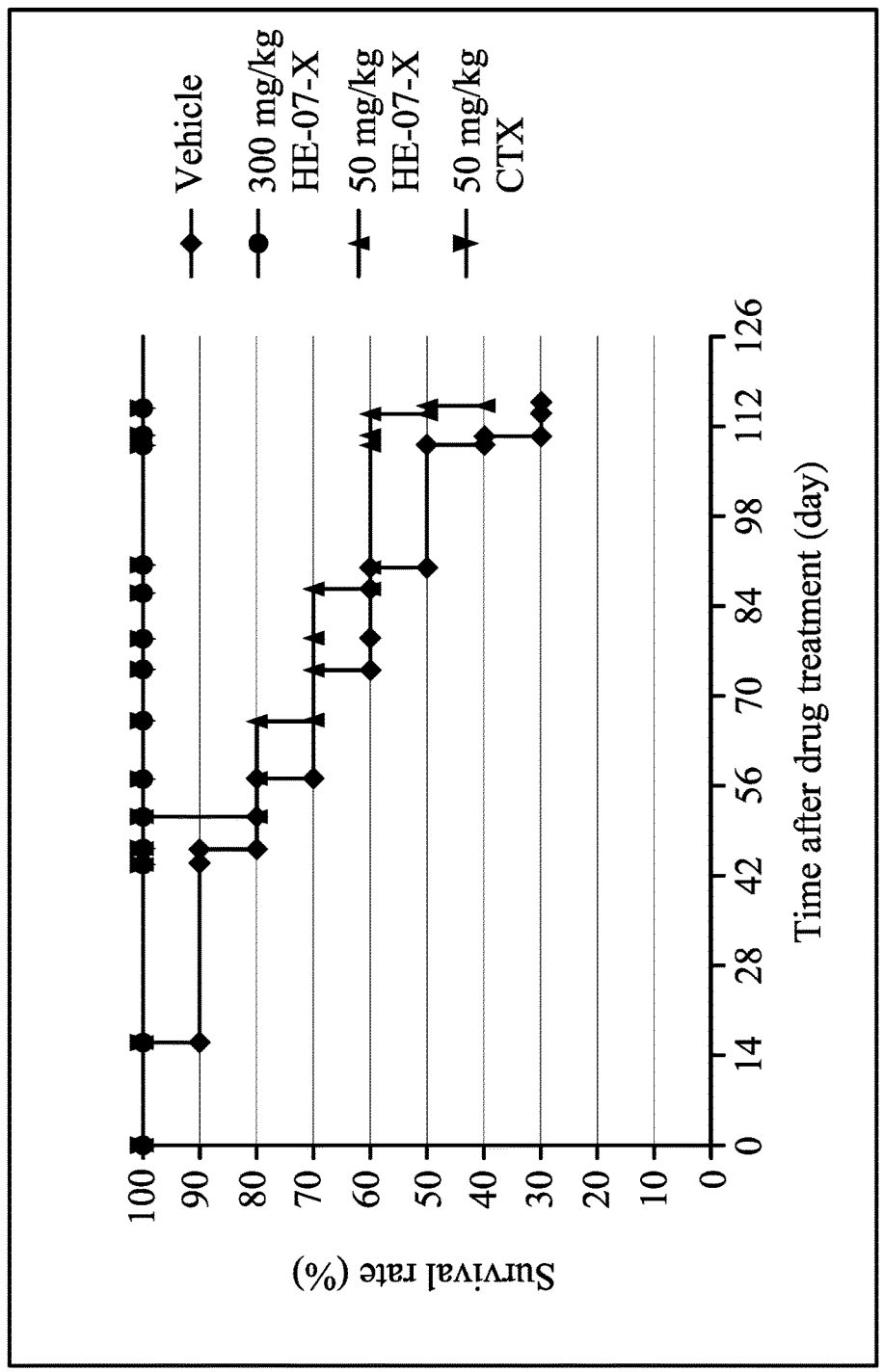
FIG. 8B shows the effects of the active fraction HE-07-X from the ethanol extract of *Clausena lansium* on the survival rate of mice in the animal model of lupus erythematosus. Survival analysis was performed by Kaplan-Meier method and GraphPad Prism 6 software, and each group was compared with the vehicle group, and the results show that the 300 mg/kg HE-07-X group and the 50 mg/kg CTX group both have significant differences with vehicle group (*p<0.01).

Effects of the active fraction HE-07-X on NZBWF 1/J mice were determined by Method 6 mentioned above. The results are shown in FIGS. 8A and 8B and Table 8, and FIGS. 9A to 9C.

TABLE 8

Effects of the active fraction HE-07-X on the survival rate of NZBWF1/J mice

| Drug to be tested | Survival rate (%) | Statistical analysis |
|---|---|---|
| Vehicle | 30 | |
| 300 mg/kg HE-07-X | 100 | 0.0011* |
| 50 mg/kg HE-07-X | 40 | 0.5187 |
| 50 mg/kg Cyclophosphamide (CTX) (Drug for clinical treatment for lupus erythematosus) | 100 | 0.002* |

Kaplan-Meier method

FIG. 8A shows that in the animal model of lupus erythematosus, administration of 300 mg/kg of the active fraction HE-07-X is capable of stably increasing the body weights of the mice.

Moreover, according to FIG. 8B and Table 8, it is clearly known that in the animal model of lupus erythematosus, administration of 300 mg/kg of the active fragment HE-07-X is capable of dramatically increasing the survival rate of the mice.

Figure 9A:
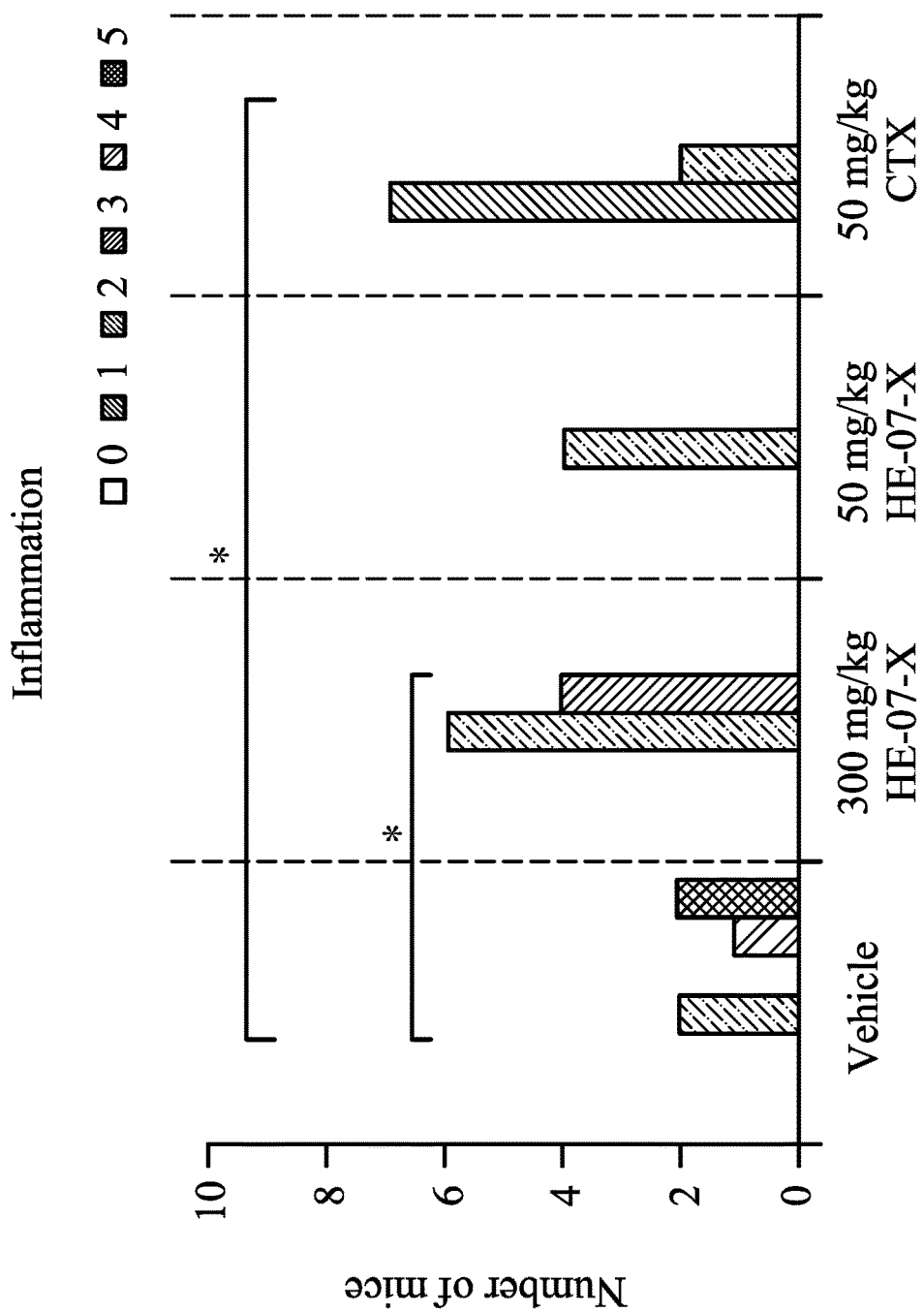
FIG. 9A shows the effects of the active fraction HE-07-X from the ethanol extract of *Clausena lansium* on kidney inflammation, tubular degeneration and glomerulonephritis in the animal model of lupus erythematosus. Chi square Test, *p<0.05 (compared with vehicle treatment).
Figure 9B:
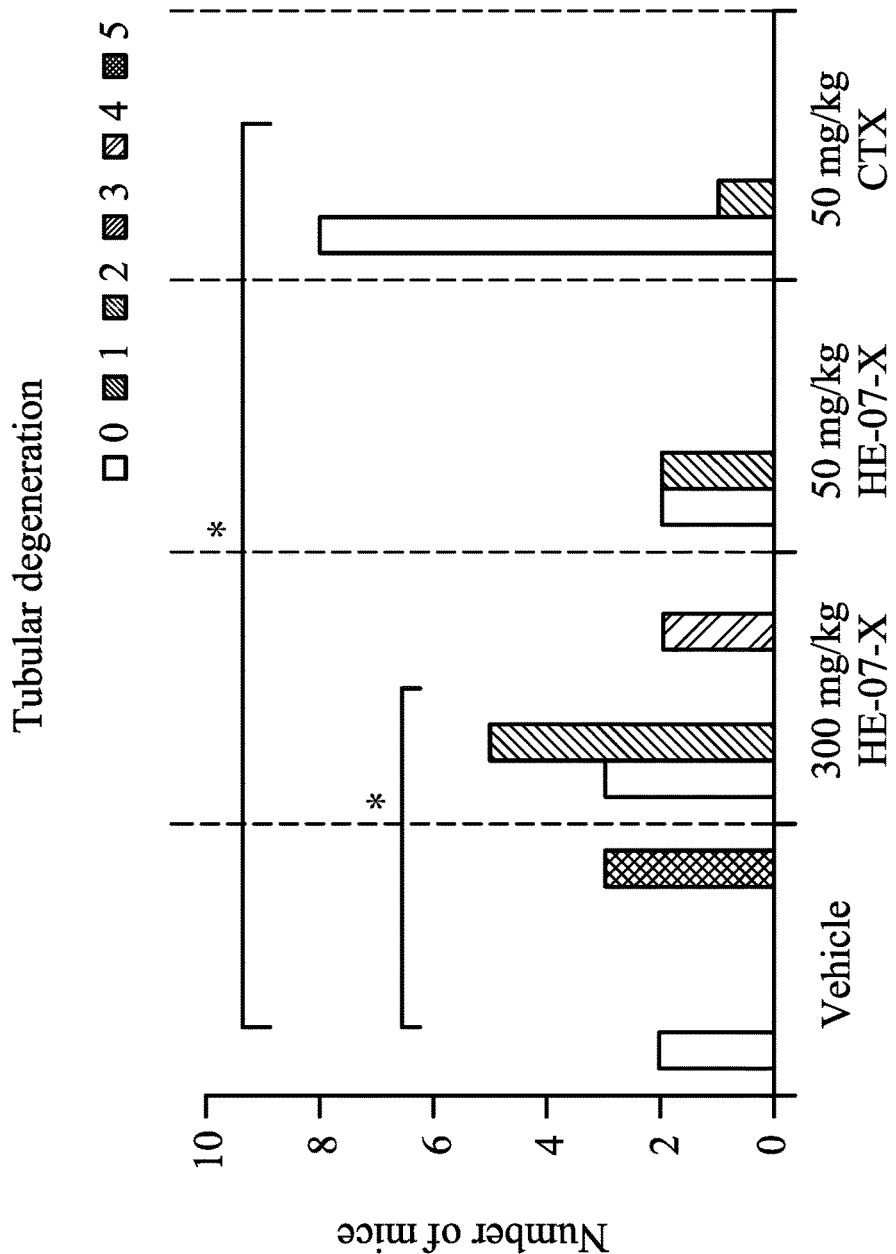
FIG. 9B shows the effects of the active fraction HE-07-X from the ethanol extract of *Clausena lansium* on tubular degeneration in the animal model of lupus erythematosus. Chi square Test, *p<0.05 (compared with vehicle treatment).
Figure 9C:
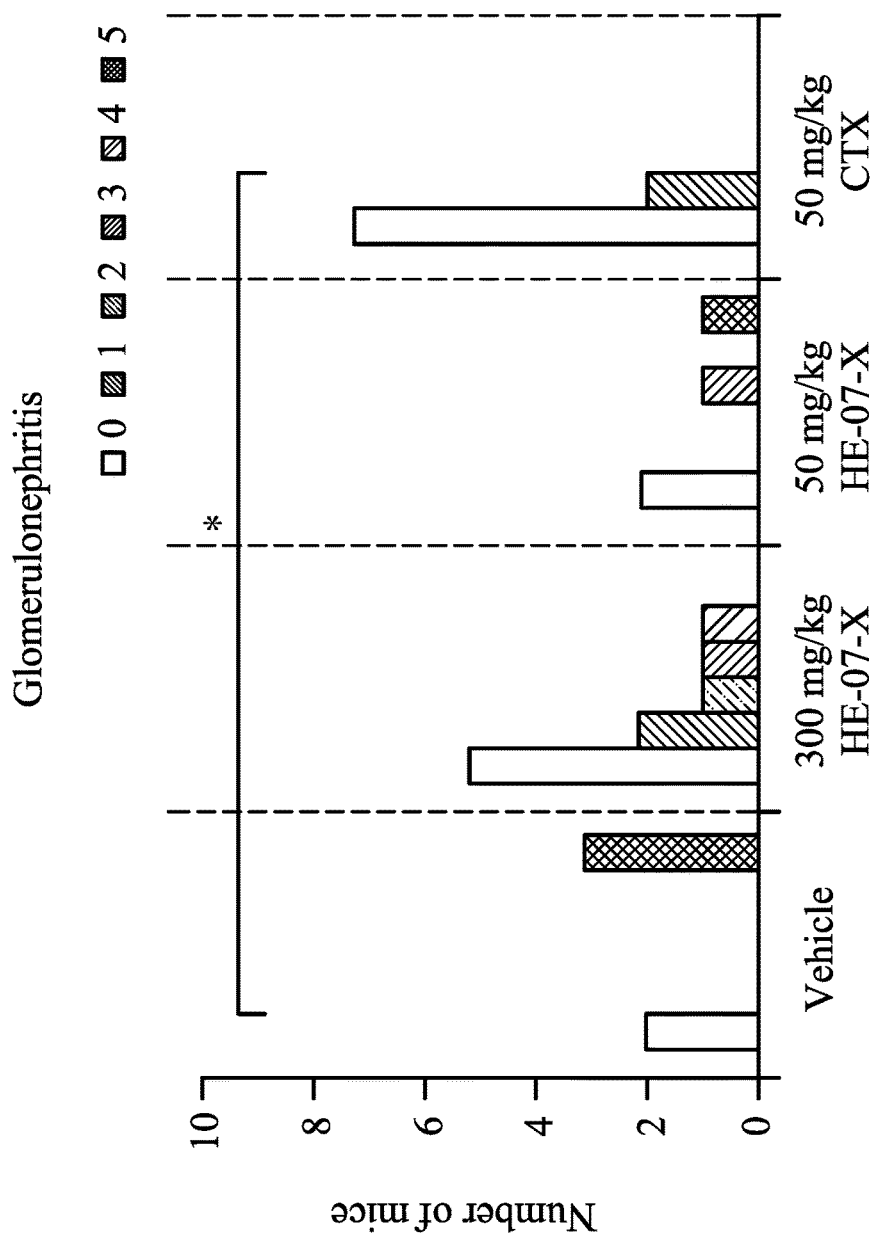
FIG. 9C shows the effects of the active fraction HE-07-X from the ethanol extract of *Clausena lansium* on glomerulonephritis in the animal model of lupus erythematosus. Chi square Test, *p<0.05 (compared with vehicle treatment).

Based on FIGS. 9A to 9C, it is known that in the animal model of lupus erythematosus, administration of 300 mg/kg of the active fraction HE-07-X is capable of alleviating kidney inflammation and significantly reducing tubular degeneration and glomerulonephritis.

Since the active fraction HE-07-X from the ethanol extract of Clausena lansium can effectively alleviate nephritis and raise the survival rate of NZBWF1/J mice that is commonly used as the lupus erythematosus animal model, it could apply the HE-07-X to the treatment of lupus erythematosus and lupus nephritis.

(C) Active Ingredients of the Ethanol Extract of Clausena lansium and Effects Thereof The respective effects of 5 compounds of the above-mentioned 6 compounds present in the active fraction HE-07-X, which have higher contents, F7m, F6m, F5m, F4m and F3m, were further determined.

1. Effects of Compounds Present in the Active Fraction HE-07-X from the Ethanol Extract of Clausena lansium on IL-17 Secretion in Peripheral Blood Leukocytes (PBLs) and EL4 Cells Effects of compounds in the active fraction HE-07-X on IL-17 secretion in peripheral blood leukocytes (PBLs) and EL4 cells were determined through Method 2 and Method 8 mentioned above, respectively. The results are shown in Table 9.

TABLE 9

Effects of compounds in the active fraction HE-07-X on IL-17 secretion in peripheral blood leukocytes (PBLs) and EL4 cells

| | $IC_{50}$ (μg/ml) IL-17 inhibition | |
|---|---|---|
| Drug to be tested | Peripheral blood leukocyte (PBL) | EL4 cells |
| F3m | 2.4 | 2.8 |
| F4m | 4.3 | 15.9 |
| F5m | 20.5 | 45.0 |
| F6m | 3.0 | 5.1 |
| F7m | 28.7 | 47.2 |

Based on the results shown in Table 9, 6 compounds isolated from Clausena lansium, F3m (indizoline), F4m (8-geranyloxypsoralen), F5m (imperatorin), F6m (ζ-clausenamide) and F7m (prangenin) have inhibitory activities on IL-17 secretion.

Since F3m (indizoline), F4m (8-geranyloxypsoralen), F5m (imperatorin), F6m (ζ-clausenamide) and F7m (prangenin) are capable of inhibiting IL-17 secretion and it has been clinically proven that a monoclonal antibody of IL-17 has a significant effect on treating the above-mentioned autoimmune diseases, they could be applied to treatment of autoimmune diseases, such as psoriasis, psoriatic arthritis, ankylosing spondylitis, lupus erythematosus, lupus nephritis, etc.

4. Effects of Compounds Present in the Active Fragment HE-07-X from the Ethanol Extract of *Clausena lansium* on Production of the Acute Inflammatory Factors, TNF-α, IL-6 and MCP-1 in the Model of Lipopolysaccharide-Induced Acute Inflammation in Mice Effects of compounds in the active fraction HE-07-X on production of the acute inflammatory factors, TNF-α, IL-6 and MCP-1 in the model of lipopolysaccharide-induced acute inflammation in mice were determined by Method 5 mentioned above. The results are shown in FIGS. 10A and 10B, FIGS. 11A and 11B, and FIGS. 12A and 12B, respectively.

Figure 10A:
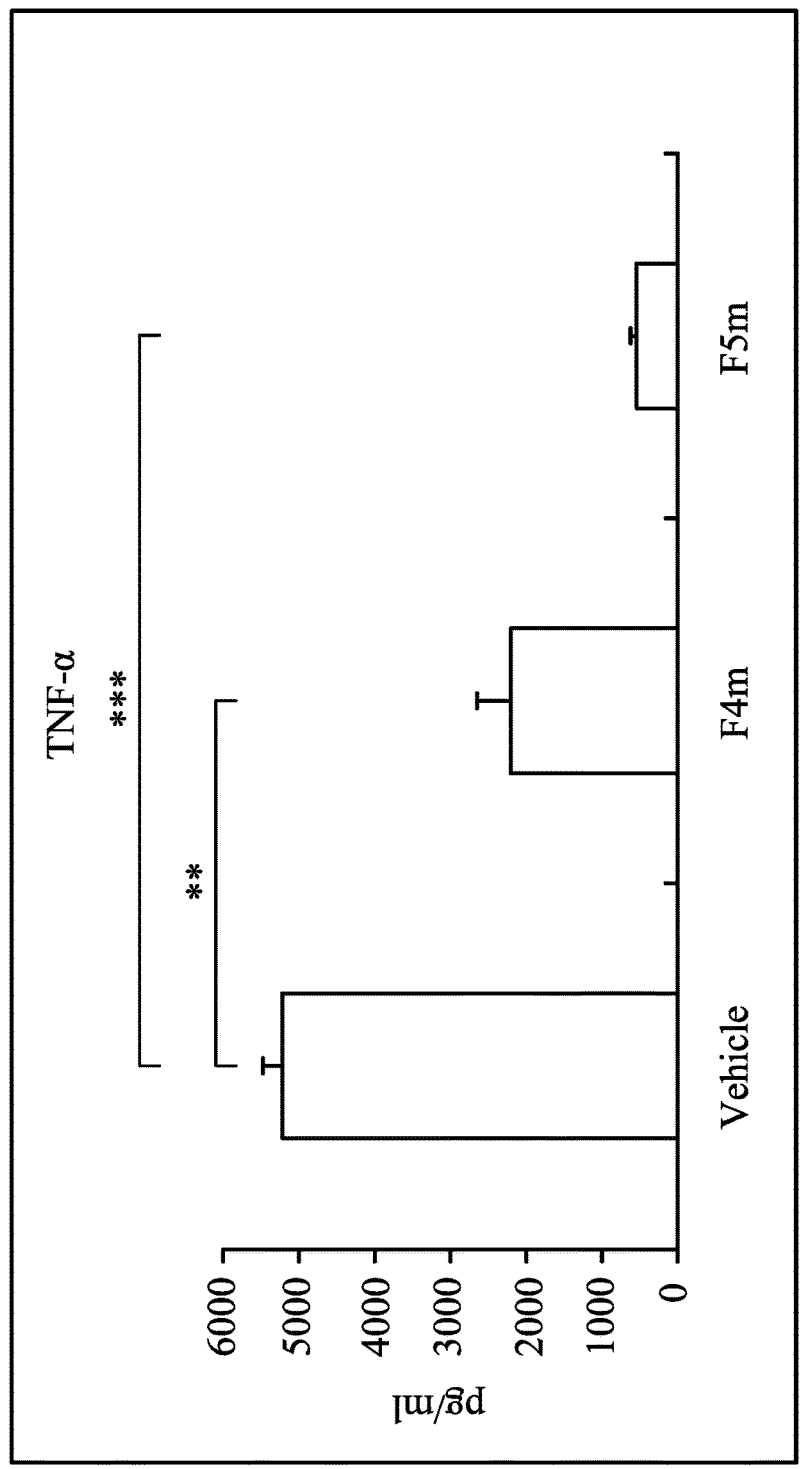
FIGS. 10A and 10B show the effects of compounds in the active fraction HE-07-X from the ethanol extract of *Clausena lansium,* F4m, F5m, F3m and F6m, on production of the acute inflammatory factor, TNF-α, in the model of lipopolysaccharide-induced acute inflammation in mice. n=5, the results are shown as Mean±Standard Deviation: Student's t-test, p<0.01; *p<0.001 (compared with vehicle treatment).
Figure 10B:
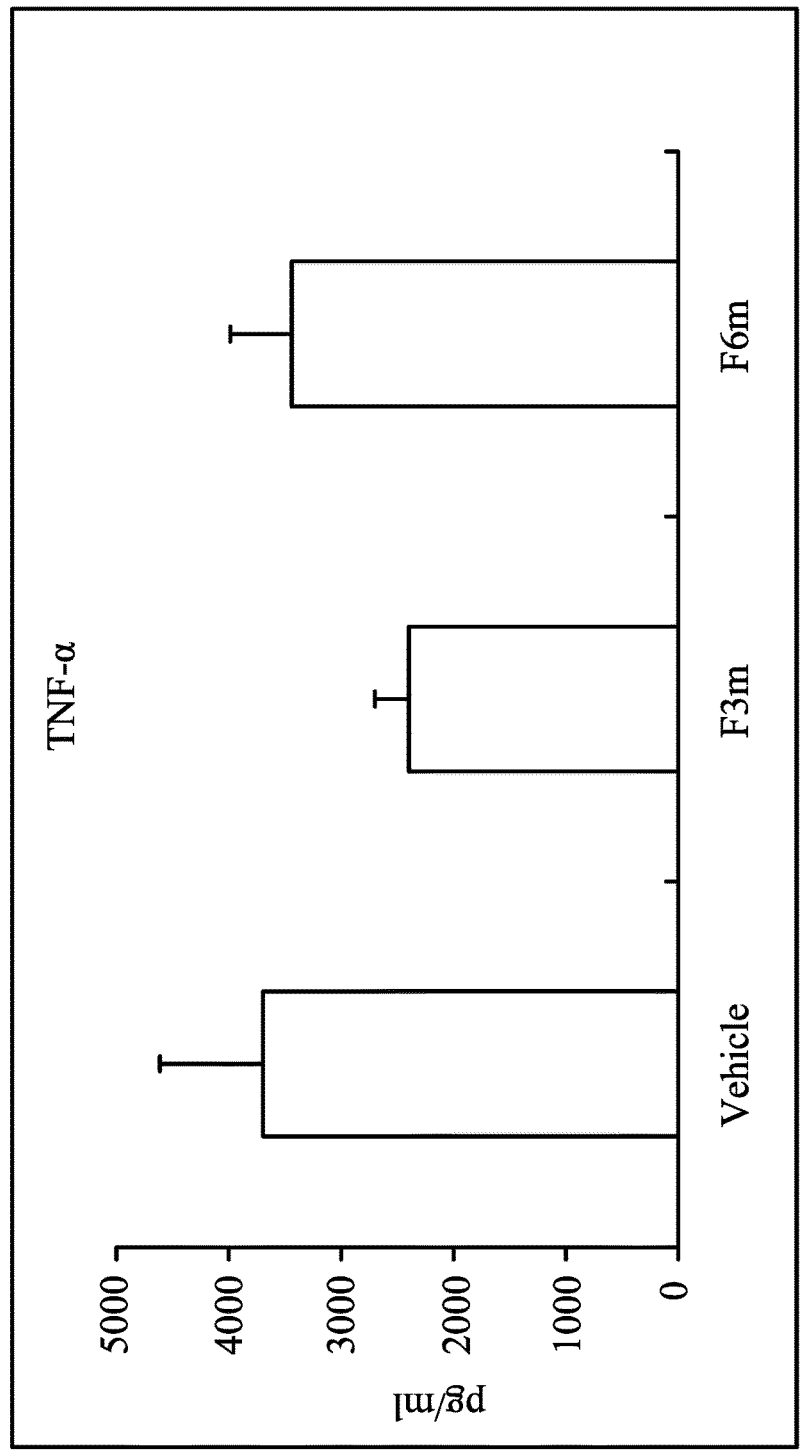
Figure 11A:
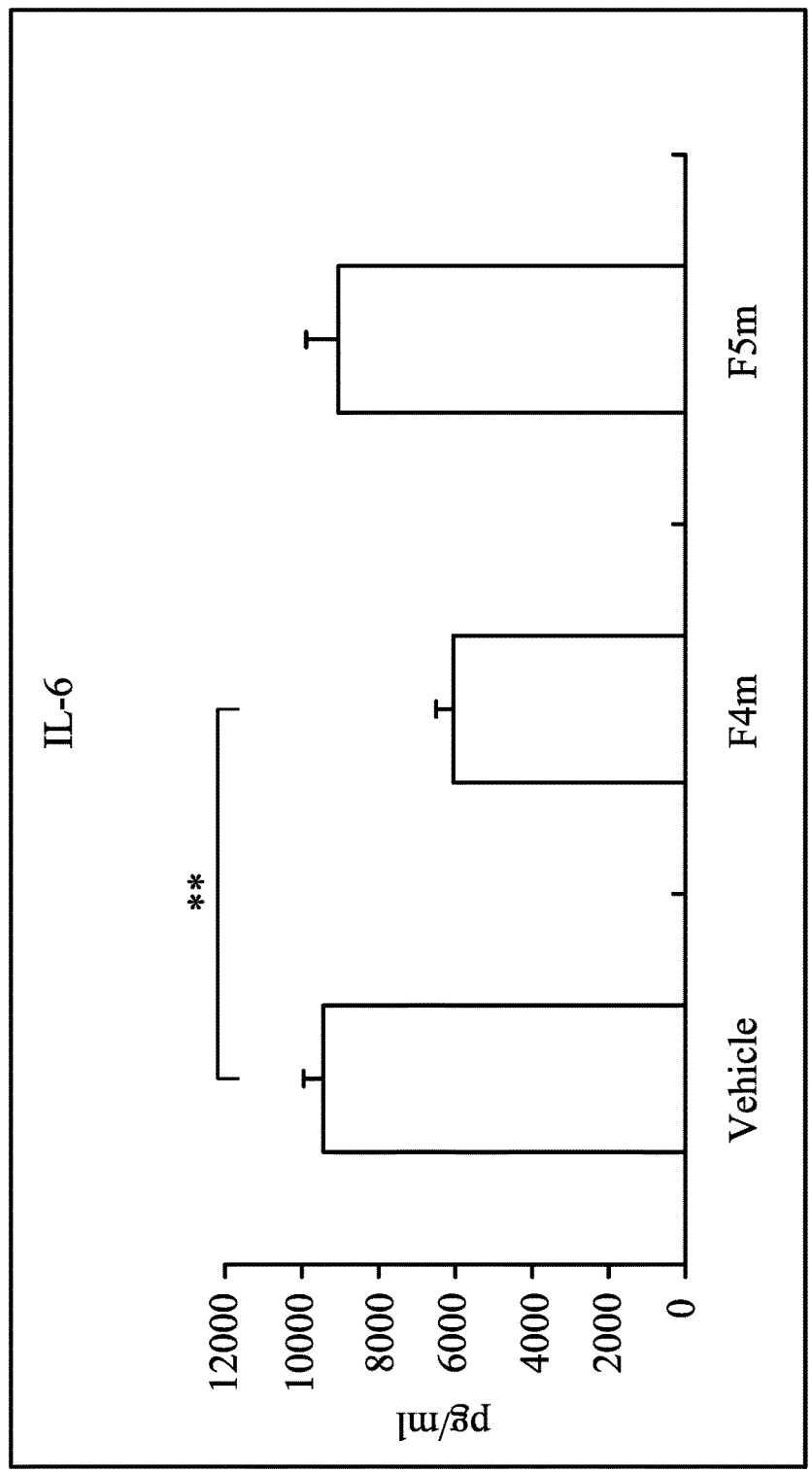
FIGS. 11A and 11B show the effects of compounds in the active fraction HE-07-X from the ethanol extract of *Clausena lansium,* F4m, F5m, F3m and F6m, on production of the acute inflammatory factor, IL-6, in the model of lipopolysaccharide-induced acute inflammation in mice. n=5, the results are shown as Mean±Standard Deviation: Student's t-test, *p<0.05; **p<0.01 (compared with vehicle treatment).
Figure 11B:
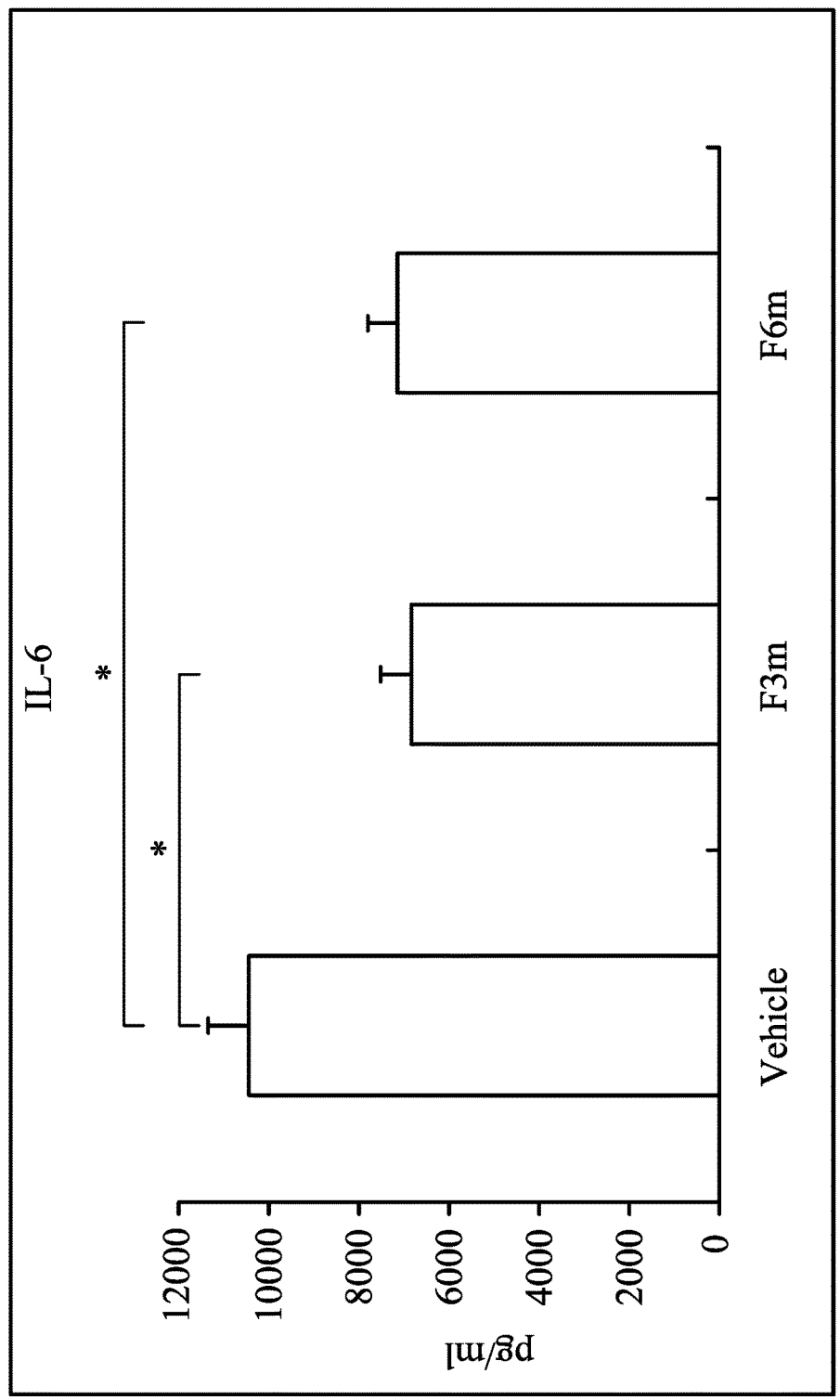
Figure 12A:
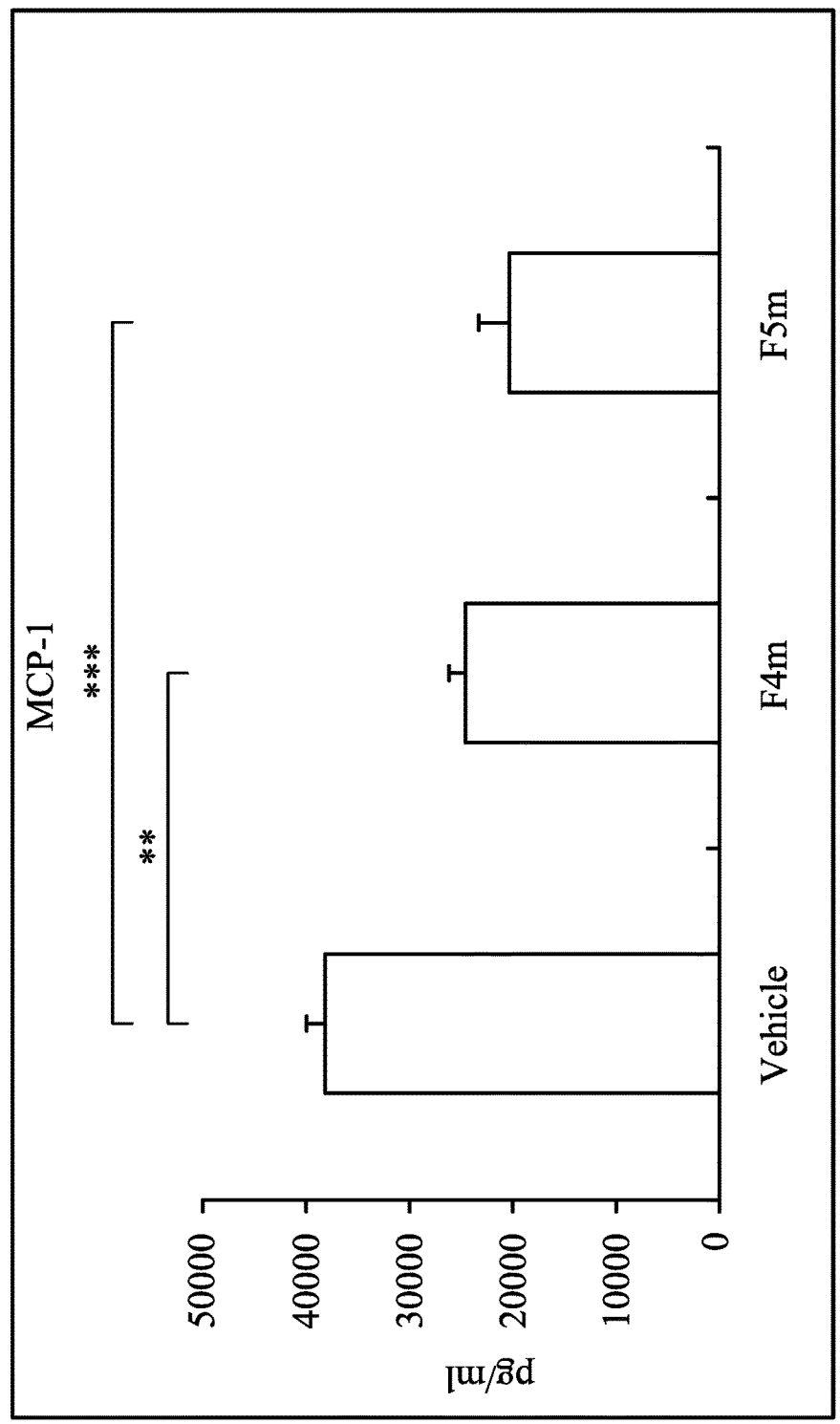
FIGS. 12A and 12B show the effects of compounds in the active fraction HE-07-X from the ethanol extract of *Clausena lansium,* F4m, F5m, F3m and F6m, on production of the acute inflammatory factor, MCP-1, in the model of lipopolysaccharide-induced acute inflammation in mice. n=5, the results are shown as Mean±Standard Deviation: Student's t-test, p<0.01; *p<0.001 (compared with vehicle treatment).
Figure 12B:
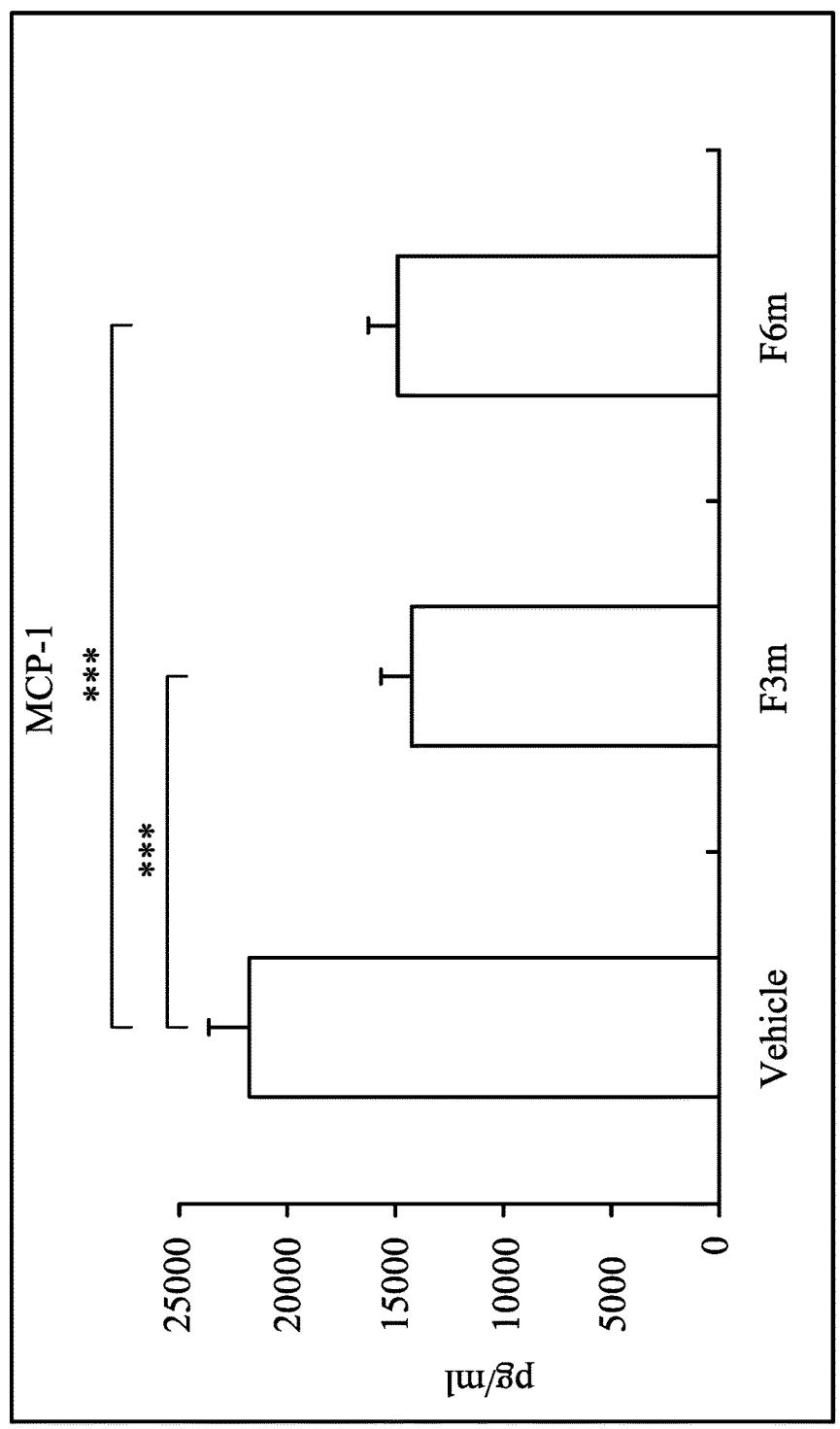

FIGS. 10A and 10B show that in the model of lipopolysaccharide-induced acute inflammation in mice, F4m and F5m are capable of significantly inhibiting the production of the inflammatory factor, TNF-α. FIGS. 11A and 11B show that in the model of lipopolysaccharide-induced acute inflammation in mice, F4m, F3m and F6m are capable of significantly inhibiting the production of the inflammatory factor, IL-6. Moreover, FIGS. 12A and 12B show that in the model of lipopolysaccharide-induced acute inflammation in mice, F4m, F5m, F3m and F6m are all capable of significantly inhibiting the production of the inflammatory factor, MCP-1.

According to the results mentioned above, it is known that, in the 6 compounds which are isolated from *Clausena lansium*, F3m (indizoline), F4m (8-geranyloxypsoralen), F5m (imperatorin) and F6m (ζ-clausenamide) have anti-inflammation activities.

Since F3m (indizoline), F4m (8-geranyloxypsoralen), F5m (imperatorin) and F6m (ζ-clausenamide) have significant inhibiting effects on TNF-α, IL-6 and MCP-1, they could be applied to treatment or alleviation of autoimmune diseases, such as rheumatoid arthritis, juvenile idiopathic arthritis, Crohn's disease, ulcerative colitis (UC), lupus erythematosus, lupus nephritis, etc.

Figure 13:
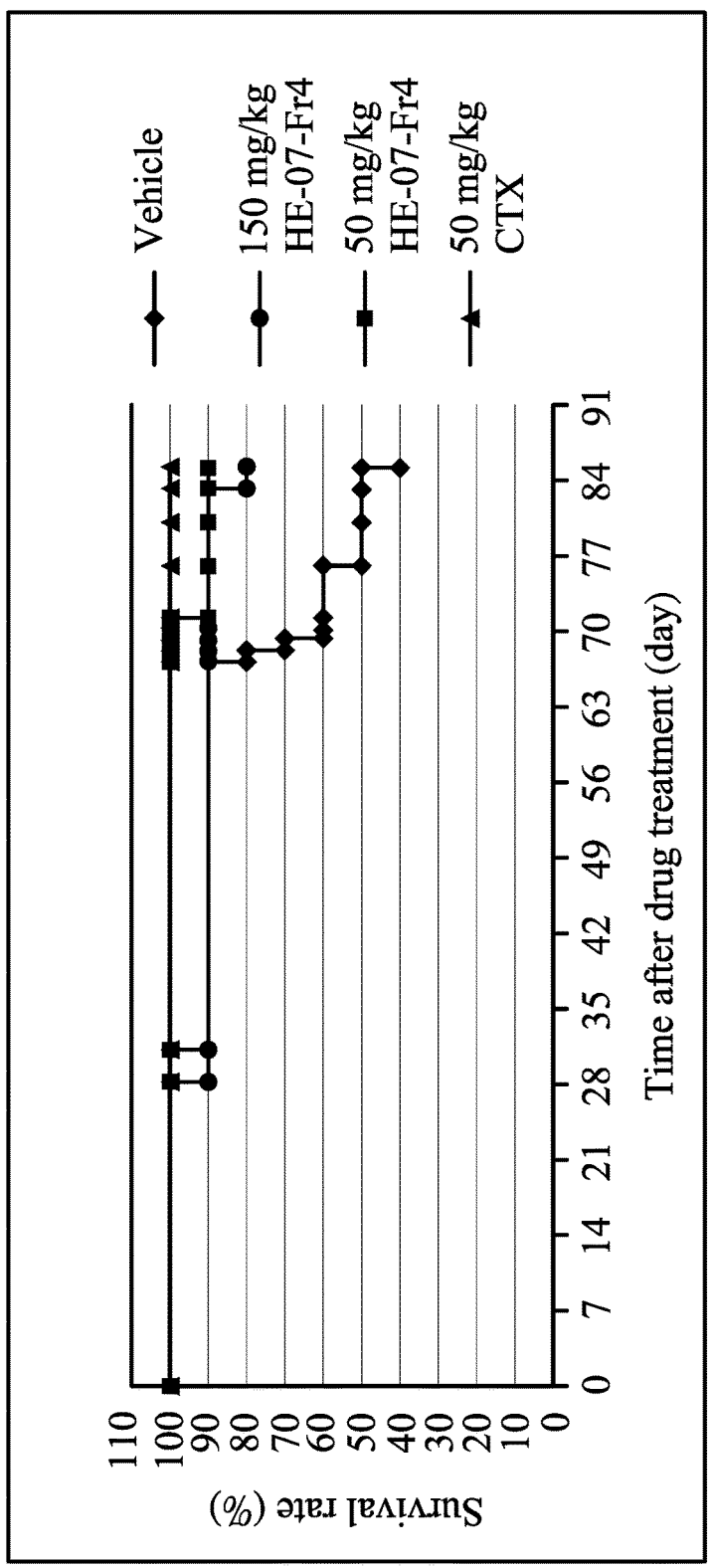
FIG. 13 shows the effects of the active fraction HE-07-Fr4 (containing greater than 80% of F4m) from the ethanol extract of *Clausena lansium* on the survival rate of mice in the animal model of lupus erythematosus. Survival analysis was performed by Kaplan-Meier method and GraphPad Prism 6 software, and each group was compared with the vehicle group, and the results show that the 50 mg/kg HE-07-Fr4 group and the vehicle group have significant differences (p<0.05), and the 50 mg/kg CTX group and the vehicle group also have significant differences (p<0.01).

5. Effects of Compounds Present in the Active Fraction HE-07-X from the Ethanol Extract of *Clausena lansium* on NZBWF1/J Mice Effects of compounds present in the active fraction HE-07-X from the ethanol extract of *Clausena lansium* on NZBWF1/J mice were determined by Method 6 mentioned above. The results are shown in FIG. 13 and Table 10.

TABLE 10

Effects of the active fraction HE-07-Fr4 (containing more than 80% of F4m) on the survival rate of NZBWF1/J mice

| Drug to be tested | Survival rate (%) | Statistical analysis |
| --- | --- | --- |
| Vehicle | 40 | |
| 150 mg/kg HE-07-Fr4 | 80 | 0.0827 |
| 50 mg/kg HE-07-Fr4 | 90 | 0.0195* |
| 50 mg/kg cyclophosphamide (CTX) (Drug for clinical treatment for lupus erythematosus) | 100 | 0.0099* |

Kaplan-Meier method

FIG. 13 and Table 10 show that in the animal model of lupus erythematosus, administration of 50 mg/kg of the active fragment HE-07-Fr4 (containing more than 80% of F4m (8-geranyloxypsoralen)) for 12 weeks is capable of dramatically increasing the survival rate of the mice.

Since F4m (8-geranyloxypsoralen) is capable of effectively improving the survival rate of NZBWF1/J mice in the animal model of lupus erythematosus, it could be applied to the treatment of lupus erythematosus.

(D) Effects of Ethanol Extracts of Plants Belonging to Rutaceae

Method 1 mentioned above was performed on other plants belonging to Rutaceae to obtained respective ethanol extracts. The above-mentioned other plants belonging to Rutaceae were *Clausena excavata* Burm. f which belongs to *Clausena*, *Murraya paniculata* and *Murraya euchrestifolia* which belong to *Murraya*, and *Citrus grandis* and *Citrus tankan* which belong to *Citrus*.

Effects of ethanol extracts of other plants belonging to Rutaceae on IL-17 secretion in EL4 cells were determined by Method 8 mentioned above. The results are shown in Table 11.

TABLE 11

Effects of ethanol extracts of other plants belonging to Rutaceae on IL-17 secretion in EL4 cells

| Plants belonging to Rutaceae | | $IC_{50}$ (μg/ml) IL-17 inhibition |
| --- | --- | --- |
| Genus | Plant name | EL4 cells |
| *Clausena* | *Clausena excavata* Burm. f. | 212 |
| *Murraya* | *Murraya paniculata* | 25 |
| | *Murraya euchrestifolia* | 86 |
| *Citrus* | *Citrus grandis* | 86 |
| | *Citrus tankan* | 37 |

Based on Table 11, it is known that, ethanol extracts of the taxonomically close species of *Clausena lansium* which are *Clausena excavata* Burm. f. which belongs to *Clausena*, *Murraya paniculata* and *Murraya euchrestifolia* which belong to *Murraya*, and *Citrus grandis* and *Citrus* tankan which belong to *Citrus*, all are capable of inhibiting EL4 cells secreting IL-17.

Since ethanol extracts of *Clausena excavata* Burm. f. which belongs to *Clausena*, *Murraya paniculata* and *Murraya euchrestifolia* which belong to *Murraya*, and *Citrus grandis* and *Citrus* tankan which belong to *Citrus*, all are capable of inhibiting IL-17 secretion, and it has been clinically proven that a monoclonal antibody of IL-17 has a significant effect in treating the above-mentioned autoimmune diseases, they could be applied to treatment of autoimmune diseases, such as psoriasis, psoriatic arthritis, ankylosing spondylitis, lupus erythematosus, lupus nephritis, etc.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for treating a human suffering from psoriasis, psoriatic arthritis, ankylosing spondylitis, juvenile idiopathic arthritis, Crohn's disease or ulcerative colitis comprising administering a therapeutically effective amount of a *clausena lansium* extract to said human in need thereof to effectively treat the psoriasis, psoriatic arthritis, ankylosing spondylitis, juvenile idiopathic arthritis, Crohn's disease or ulcerative colitis, 2. The method of claim 1, wherein the *clausena lansium* extract contains (a) a compound having Formula (I):

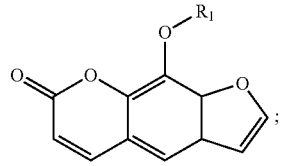

Formula (I)

(b) a compound having Formula (II):

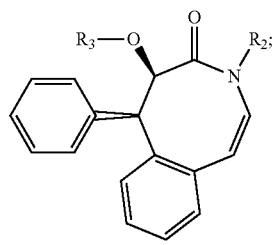

Formula (II)

and (c) a compound having Formula (III):

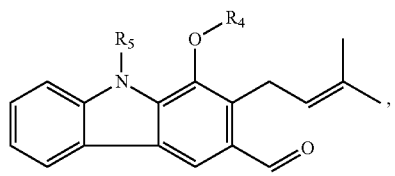

Formula (III)

wherein $R_1$ is $C_1$-$C_5$ alkyl,

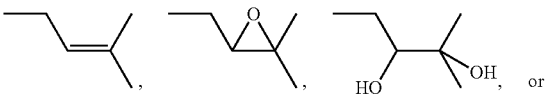 or

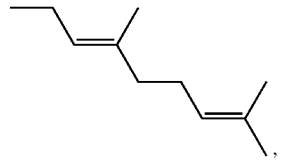

$R_2$ is H or $C_1$-$C_3$ alkyl, $R_3$ is H or $C_1$-$C_3$ alkyl, $R_4$ is H or $C_1$-$C_3$ alkyl, and $R_5$ is H or $C_1$-$C_3$ alkyl.

3. The method of claim 2, wherein the compound having Formula (I) is prangenin, imperatorin or 8-geranyloxypsoralen.

4. The method of claim 3, wherein the compound having Formula (I) is prangenin.

5. The method of claim 3, wherein the compound having Formula (I) is imperatorin.

6. The method of claim 3, wherein the compound having Formula (I) is 8-geranyloxypsoralen.

7. The method of claim 2, wherein the compound having Formula (II) is ζ-clausenamide.

8. The method of claim 2, wherein the compound having Formula (III) is indizoline.

* * * * *